US006916665B2

(12) United States Patent
Bayley et al.

(10) Patent No.: US 6,916,665 B2
(45) Date of Patent: Jul. 12, 2005

(54) BIOSENSOR COMPOSITIONS AND METHODS OF USE

(75) Inventors: Hagan P. Bayley, College Station, TX (US); Stefan G. Howorka, College Station, TX (US); Liviu Movileanu, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 09/781,697

(22) Filed: Feb. 12, 2001

(65) Prior Publication Data

US 2002/0094526 A1 Jul. 18, 2002

Related U.S. Application Data

(60) Provisional application No. 60/182,097, filed on Feb. 11, 2000.

(51) Int. Cl.[7] .......................... C12Q 1/70; G01N 27/00; C07K 14/00
(52) U.S. Cl. ..................... 436/149; 435/5; 435/6; 435/7.1; 435/7.4; 436/149; 436/150; 436/501; 530/350; 530/825
(58) Field of Search ..................... 435/4, 6, 7.2, 287.1, 435/287.2; 436/86, 518, 528, 531; 422/50, 68.1, 82.01, 99; 530/350

(56) References Cited

U.S. PATENT DOCUMENTS

| 5,234,566 A | * | 8/1993 | Osman et al. ......... 204/403.06 |
| 5,368,712 A | | 11/1994 | Tomich et al. ............... 204/403 |
| 5,443,955 A | * | 8/1995 | Cornell et al. ........... 435/317.1 |
| 5,795,782 A | * | 8/1998 | Church et al. ................. 435/4 |

FOREIGN PATENT DOCUMENTS

| WO | WO 96 20688 A | 7/1996 |
| WO | WO 97 20203 A | 6/1997 |
| WO | WO 99 05167 A | 2/1999 |

OTHER PUBLICATIONS

Braha et al., Designed protein pores as components for biosensors, 1997, Chemistry and Biology, 4(7):497–505.*

(Continued)

*Primary Examiner*—Padmashri Ponnaluri
*Assistant Examiner*—My-Chau T Tran
(74) *Attorney, Agent, or Firm*—Howrey LLP

(57) ABSTRACT

Provided are pore-subunit polypeptides covalently linked to one or more sensing moieties, and uses of these modified polypeptides to detect and/or measure analytes or physical characteristics within a given sample.

14 Claims, 11 Drawing Sheets

OTHER PUBLICATIONS

Thomas Ferenci and King–Sang Lee; Department of Microbiology, University of Sydney; "*Channel Architecture in Maltoporin: Dominance Studies lamb Mutations Influencing Maltodextrin Binding Provide Evidence for Independent Selectivity Filters in Each Subunit*"; Jun. 13, 1988; 7 pages.

Charles A. Roessner and Garret M. Ihler; Department of Medical Biochemistry and Genetics, Texas A&M College of Medicine; "*Formation of Transmembrane Channels in Liposomes during injection of DNA*"; Jun. 3, 1985; pp. 386–390.

Cornell E.A.: "*The gramicidin–based biosensor: a functional nano–machine*" Novartis Foundation Symposium, vol. 225, 1999, pp. 231–254, XP001052820 Chichester.

Bayley: "*Designed membrane channels and pores*" Current Opinion in Biotechnology, vol. 10. 1999, pp. 94–103, XP001058234.

Boehmer, Volker: "*Calixarenes macrocycles with (almost) unlimited possibilites*" Angew, Chem., Int. Ed. Engl. (1995). 34(7), 713–45, XP002188229.

Movileanu L. Et al.; "*Detecting protein analytes that modulate transmembrane movement of a polymer chain within a single protein pore.*" Nature Biotechnology, (Oct. 2000) 18 (10) 1091–5.; XP002188230.

Van Der Goot E.A.: "*Sensing proteins outside of the box*" Nature Biotechnology, vol. 18, Oct. 18, 2000, p. 1037 XP002188231.

Howorka: "*A protein pore with a single polymer chain tethered within the lumen*" Journal of the American Chemical Society, vol. 122, No. 11, Mar. 22, 2000, pp. 2411–2416, XP002188232 DC US.

Search Report for application PCT/US01/04482, European Patent Office, Feb. 2, 2002, PCT.

\* cited by examiner

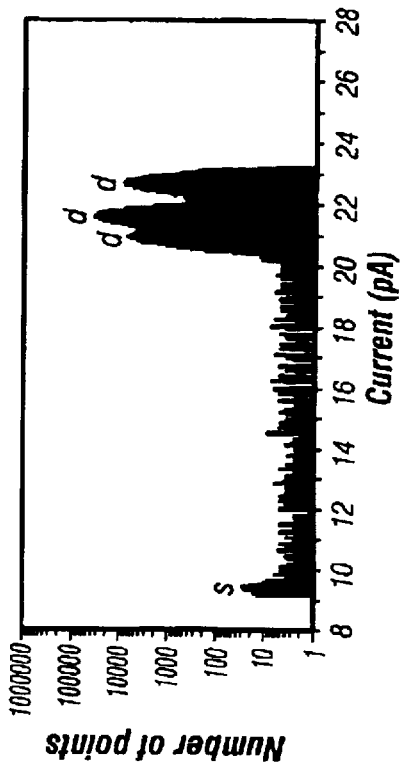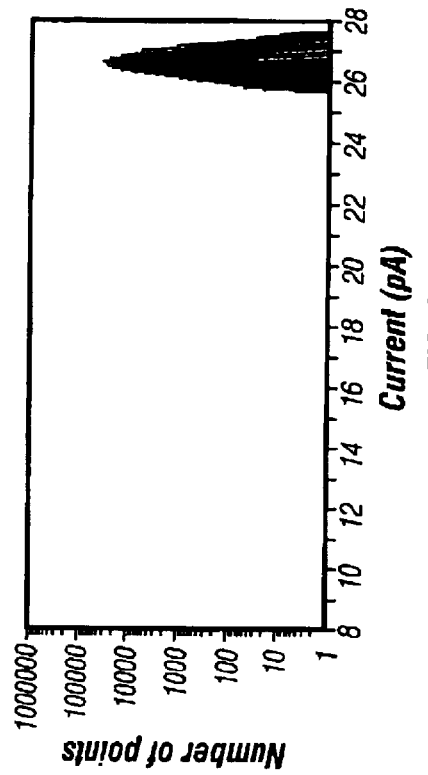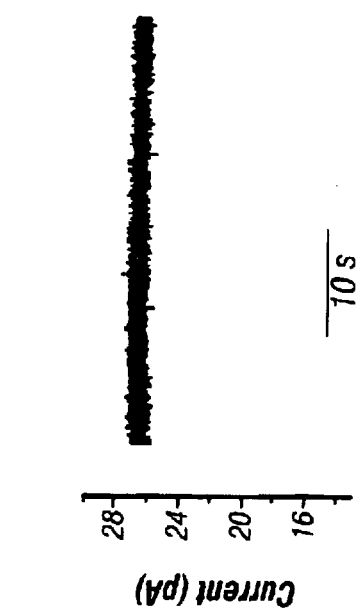
FIG. 2A
FIG. 2B
FIG. 2C
FIG. 2D

*DNA-oligonucleotides*
—— Oligo-A 5'-CATTCACC-3' SEQ ID NO 1
······ Oligo-B 3'-GTAAGTGG-5' SEQ ID NO 2
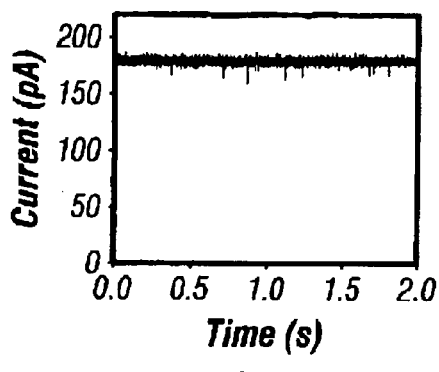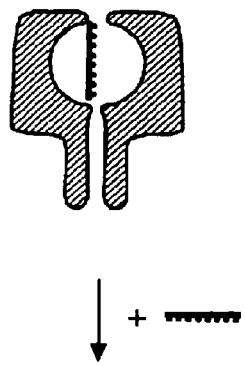
FIG. 7A-1  FIG. 7A-2
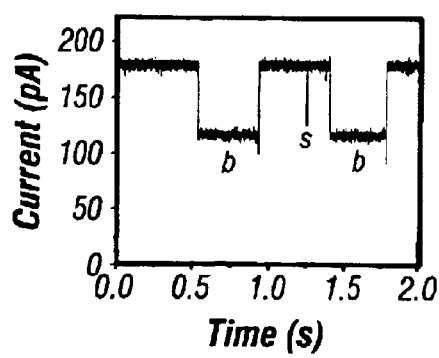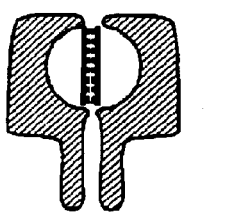
FIG. 7B1  FIG. 7B2
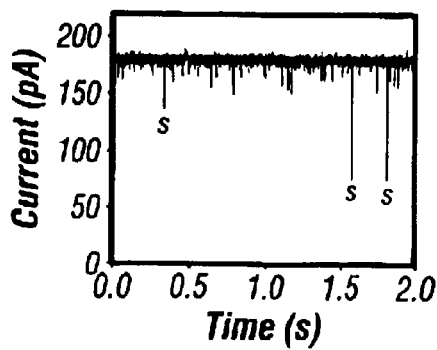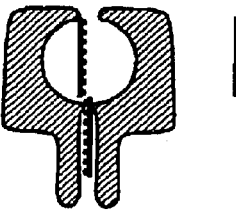
FIG. 7C-1  FIG. 7C-2

BIOSENSOR COMPOSITIONS AND METHODS OF USE

The present application claims priority to U.S. provisional application Ser. No. 60/182,097, filed Feb. 11, 2000, the entire specification, claims and drawings of which are incorporated herein by reference without disclaimer.

The U.S. government owns rights in the present invention pursuant to grant number DE-FG0397ER20271 from the Department of Energy, grant number C98-00656 from the Air Force Office of Scientific Research, Multi-Disciplinary Research Program of the University Research Initiative (AFOSR, MURI), grant number N00014-99-1-0717 from the Office of Naval Research, Multi-Disciplinary Research Program of the University Research Initiative (ONR, MURI), and grant number DAPT6397-C-0015 from the Defense Advanced Research Projects Agency (DARPA).

BACKGROUND OF THE INVENTION

1. Field of the Invention

The present invention relates generally to detection of one or more analytes in a sample and/or the magnitude of or changes in physical properties of a sample. More particularly, it concerns pore-subunit polypeptides covalently linked to one or more sensing moieties, and the use of these modified polypeptides to detect and/or measure analytes or certain physical characteristics within a given sample.

2. Description of Related Art

The examination and manipulation of individual molecules is a thriving area of research. Single molecule detection methods, which include electrical recording (Hladky and Haydon, 1970; Sakmann and Neher, 1995), optical spectroscopy (Moerner and Orrit, 1999; Weiss, 1999) and force measurements (Mehta et al., 1999), can provide structural and functional information that is often difficult or impossible to obtain by conventional techniques, which measure the properties of large ensembles of molecules. Recent accomplishments include observations of the movement of individual atoms and small molecules (Gimzewski and Joachim, 1999), the movement of linear and rotary motor proteins (Mehta et al., 1999), the turnover of individual enzymes (Xie and Lu, 1999) and the unfolding and refolding of proteins (Mehta et al., 1999).

In the area of biosensors, progress has been made in developing protein channels and pores as sensor elements (Ziegler and Gopel, 1998; Bayley, 1999). According to this concept, analyte molecules modulate the ionic current passing through the pores under a transmembrane potential. For example, binding sites can be engineered into pores expressly for capturing analyte molecules, which act as partial channel blockers. Stochastic sensing, which uses currents from single pores, is an especially attractive prospect (Braha et al., 1997; Gu et al., 1999). The approach yields both the concentration and identity of an analyte, the latter from its distinctive current signature. Using certain types of stochastic sensing, the inventors have succeeded in detecting divalent metal ions (Braha et al., 1997) and a variety of organic molecules (Gu et al., 1999).

Despite the initial development of stochastic sensing, there remains in the art a need for sensing elements and systems that respond to a wider variety of analytes. The development of stochastic sensing components and systems that permit interactions with sensor elements that would not normally occur with the existing methodology would represent a significant advance in the art.

SUMMARY OF THE INVENTION

The present invention overcomes one or more of the foregoing and other shortcomings in the art by providing compositions and methods comprising improved, versatile and adaptable responsive sensing moieties for use in sensing applications, including stochastic sensing. The invention particularly provides modified pore-forming polypeptides in which a pore-subunit polypeptide is covalently linked to at least a first sensing moiety; oligomeric and polymeric pore assemblies and biosensors thereof; and methods of using such covalently modified polypeptides, pore assemblies and biosensors.

The "modified" polypeptides of the invention are "sensing" polypeptides that generally comprise a "pore-forming" or "pore-subunit" polypeptide that is covalently linked to at least a first sensing moiety. "Pore-forming" and "pore-subunit" polypeptides, as used herein, are polypeptides that are capable of forming a pore and/or those that are capable of assembling into an oligomeric or polymeric pore assembly in the presence of a plurality of pore-forming or pore-subunit polypeptides.

A "pore-forming" polypeptide for use in the invention may therefore be a polypeptide that forms a pore as a single unit or monomer. Examples of such pore-forming polypeptides include certain porins and channel proteins and polypeptides. Where the pore-forming polypeptide requires association with other pore-forming polypeptides to form a pore, the term "pore-subunit" polypeptide may be preferred, although the terms "pore-forming polypeptide" and "pore-subunit polypeptide" are used interchangeably herein unless otherwise stated or clear from the scientific context.

The "covalent attachment" of one or more sensing moieties to pore-forming or pore-subunit polypeptides to create the "modified, pore-forming, sensing pore-subunit polypeptides" of the present invention means that at least a first "exogenous" sensing moiety is covalently attached to the polypeptide. This differs from pore-subunit polypeptides in which the only modification(s) is one or more mutations within the amino acid sequence of the polypeptide itself. Although the sensing moiety is engineered into such polypeptides, in contrast to the native polypeptide sequence, such engineered, modified or "mutant" polypeptides still comprise an "endogenous" sensing moiety.

In contrast, the present invention provides modified pore-forming or pore-subunit polypeptides that at least comprise one exogenous sensing moiety that is covalently linked to the pore-subunit polypeptide. Those of ordinary skill in the art will understand that engineered, mutant or variant pore-subunit polypeptides may well be used in the invention so long as they are further "covalently attached" to at least a first sensing moiety. That is, so long as any existing amino acid mutation is not solely relied upon to provide the sensing means.

In using one or more engineered, mutant or variant pore-forming or pore-subunit polypeptides in the present invention, the modified, mutated or "heterologous" amino acid(s) may, in fact, form the point of attachment for one or more of the covalently attached sensing moieties. As such, the pore-subunit polypeptide may be engineered to produce at least a first new or heterologous "attachment site", to which the sensing moiety or moieties are subsequently covalently attached. Equally, the invention includes a range of engineered, mutant or variant pore-subunit polypeptides that comprise at least one modified, mutated or "heterologous" amino acid at a location distinct from the covalent attachment of the sensing moiety or moieties. Such heterologous amino acids may themselves impart a sensing function, so long as such a function is in addition to the sensing function provided by the covalently attached sensing moiety or moieties of the invention.

Accordingly, in certain embodiments, the invention provides a modified pore-forming or pore-subunit polypeptide other than wherein the modification of the modified pore-subunit polypeptide exists only in that the polypeptide contains a heterologous analyte-binding amino acid. In further embodiments, this invention provides oligomeric and polymeric pore assemblies and biosensors comprising at least a first modified pore-subunit polypeptide other than wherein the modification of the modified pore-subunit polypeptide exists only in that the polypeptide contains a heterologous analyte-binding amino acid. In yet further embodiments, the invention provides methods of detecting analytes, including changes in the type and/or amount of biological and chemical constituents in samples, and methods of detecting changes in the physical environment, using oligomeric and polymeric pore assemblies and biosensors that comprise at least a first modified pore-subunit polypeptide other than wherein the modification of the modified pore-subunit polypeptide exists only in that the polypeptide contains a heterologous analyte-binding amino acid.

In other embodiments, the invention provides modified pore-forming or pore-subunit polypeptides, oligomeric and polymeric pore assemblies and biosensors thereof, and methods of using such polypeptides, pore assemblies and biosensors, other than wherein the modified pore-subunit polypeptide is a mutant staphylococcal alpha hemolysin polypeptide and wherein the modification exists only in that the polypeptide comprises a heterologous analyte-binding amino acid, which polypeptide assembles into an analyte-responsive heteroheptameric pore assembly in the presence of a wild type staphylococcal alpha hemolysin polypeptides.

In yet other embodiments, the invention provides modified pore-forming or pore-subunit polypeptides, oligomeric and polymeric pore assemblies and biosensors thereof, and methods of using such polypeptides, pore assemblies and biosensors, other than wherein the modified pore-subunit polypeptide is a pore-subunit polypeptide, such as a staphylococcal alpha hemolysin polypeptide, wherein the modification exists only in that the polypeptide is attached or covalently attached to a chelating molecule for metal detection.

The modified, covalently-linked, sensing pore-forming or pore-subunit polypeptides of the invention are capable of assembling into pores, or into oligomeric and/or polymeric pore assemblies in the presence of a plurality of pore-forming or pore-subunit polypeptides. All such pores and pore assemblies are herein termed "pore assemblies" for simplicity, irrespective of whether the pore is formed by a single polypeptide or two or more such polypeptides. The formation of the pore assemblies can take place in any suitable environment, such as any suitable lipid environment, e.g., a bilayer, cell membrane, liposome and the like.

In certain preferred embodiments, the parent "pore-subunit polypeptides" and modified versions of the invention are capable of assembling into oligomeric and/or polymeric pore assemblies in the presence of a plurality of "like" pore-subunit polypeptides. This includes assemble with a plurality of unmodified and modified versions of the same pore-subunit polypeptides. Equally, the use of "pore-subunit polypeptides" capable of forming oligomeric and/or polymeric pore assemblies in the presence of distinct pore-subunit polypeptides is included within the invention.

The invention thus provides homomeric pore assemblies, in which all the pore-subunit polypeptides are modified pore-subunit polypeptides of the invention. The invention further provides a range of heteromeric pore assemblies, in which at least one of the pore-subunit polypeptides is a modified pore-subunit polypeptide of the invention, but in which the overall pore assembly includes at least one distinct type of pore-subunit polypeptide. The heteromeric pore assemblies may be further sub-divided into those heteromeric pore assemblies in which the pore-subunit polypeptides are modified and unmodified versions of the same polypeptide; and those heteromeric pore assemblies that comprise at least two pore-subunit polypeptides or different origins, whether in modified or unmodified form.

Any polypeptide, whether of natural or totally synthetic origin, may be used in the invention so long as it can be effectively covalently attached to one or more sensing moieties and so long as it meets the pore-forming criteria described herein and known those of ordinary skill in the art. Exemplary pore-forming polypeptides are the pore-subunit polypeptides known in nature, such as bacterial pore-subunit polypeptides.

For example, certain preferred pore-forming and pore-subunit polypeptides for use in the invention include, but are not limited to, porins, complement pore polypeptides, hemolysin C polypeptides, streptolysin O polypeptides and membrane channel polypeptides, such as potassium channel polypeptides. In certain preferred embodiments of the invention, the pore-subunit polypeptide is a staphylococcal hemolysin polypeptide, with staphylococcal alpha hemolysin polypeptides being particularly preferred.

As described above, the invention contemplates the use of engineered, mutant and variant pore-forming or pore-subunit polypeptides, including those with heterologous amino acid(s), so long as an exogenous sensing moiety is covalently attached. As such, in certain preferred embodiments, the pore-subunit polypeptides of the invention are mutant staphylococcal alpha hemolysin polypeptides that comprise at least a first heterologous amino acid. For example, such as wherein the mutant staphylococcal alpha hemolysin polypeptide comprises a cysteine residue in place of serine at position 106 of the wild-type staphylococcal alpha hemolysin polypeptide; or wherein the mutant staphylococcal alpha hemolysin polypeptide comprises a cysteine residue in place of lysine at position 8 of the wild-type staphylococcal alpha hemolysin polypeptide.

The modified pore-forming or pore-subunit polypeptides are "covalently linked or attached" to at least a first sensing moiety in any manner that substantially preserves the ability of the polypeptide to assemble into oligomeric and/or polymeric pore assemblies and that substantially preserves the ability of the sensing moiety to provide a useful sensing function.

The sensing moiety or moieties may be covalently linked to the pore-forming or pore-subunit polypeptide so that they occupy a position in a transmembrane channel, project into the lumen of, or occupy a position in a stem domain of the resultant oligomeric and/or polymeric pore assembly. The sensing moiety or moieties may also be covalently linked to a surface position on the pore-forming or pore-subunit polypeptide, so that they occupy a position close to the entrance to the channel or pore, as exemplified by the attached oligonucleotides disclosed herein.

The "covalent linkage" can be formed by one or more covalent bonds between the pore-forming or pore-subunit polypeptide and the sensing moiety or moieties. Direct covalent attachment is preferred in various aspects. However, "covalent linkage" also includes other functional chemical attachments, and does not exclude the use of linkers, such as short chains of chemical groups or peptides, which covalently link the two components without being an integral part of either component in its natural form. Synthetic linking methodology is well known in the art and can be readily adapted for use herewith in light of the inventive teaching of the present disclosure.

In certain aspects of the invention, the sensing moiety is a functional group. The term "functional group", as employed herein, is used for convenience to mean a functional sensing moiety "other than a polymer", wherein the sensing moiety provides a useful sensing function. In preferred aspects, the functional group is an "analyte-binding" functional group. In certain embodiments, the functional group binds to one or more analytes, while in other embodiments, the analyte binds to the functional group. Other functional groups are those that sense changes in the physical environment, such as changes in pH, light, voltage, temperature and the like. Although the present invention may be used in combination with radiolabels, an advantage of the invention is that radioactive substances are by no means necessary to practice the invention.

The functional group can be a naturally occurring molecule, a synthetic molecule or a combination thereof. Functional groups that are naturally occurring molecules contemplated for use in the present invention include, but are not limited to, enzyme inhibitors, haptens, nucleotides, amino acids, lipids, toxins, saccharides, chelators and/or cyclodextrins. Synthetic molecules contemplated for use in the present invention include, but are not limited to, calixarenes and/or crown ethers.

In other aspects of the present invention, the sensing moiety is a polymer. Polymers contemplated for use in the present invention can be homopolymers, heteropolymers and functionalized polymers. The polymers can also be naturally occurring molecules or synthetic molecules. In certain aspects of the invention, the polymer is polyethylene glycol (PEG) or polyethylene glycol (PEG)-biotin. In preferred aspects of the invention, the polymer is an analyte-binding polymer, including, but not limited to, oligonucleotides, polynucleotides, oligosaccharides, polysaccharides, lipopolysaccharides, proteins, glycoproteins, polypeptides and/or peptides. In particularly preferred embodiments, the attached polymer is a single-stranded oligonucleotide or polynucleotide, such as DNA or RNA.

In various embodiments of the invention, the covalently attached sensing moiety responds to a change in the type, concentration and/or amount of a biological or chemical constituent in the environment of the oligomeric pore assembly. The constituent may be an organic molecule or even a microorganism, such as a bacterium, fungi or virus. The organic molecules may be biological, physiological and/or pharmacological molecules, or may be byproducts, pollutants, environmental toxins, explosives, or such like. As such, the sensing moiety may bind to a metal or a metal ion (e.g., zinc, cobalt, copper, nickel and cadmium), a toxin, an enzyme, a nucleotide, an oligonucleotide, an amino acid, a peptide, a polypeptide, a saccharide, an oligosaccharide, a hapten, a lipid, an antibody or antigen-binding fragment thereof, or any one or more a range of organic molecules.

In still further embodiments, the sensing moiety responds to a change in the physical environment of the oligomeric pore assembly, including, but not limited to, changes in pH, light, voltage, current, resistance and/or temperature.

In additional aspects of the present invention, the pore-forming or pore-subunit polypeptide is covalently linked to at least a first and at least a second, third, fourth, etc. sensing moiety. In certain aspects, the first sensing moiety is distinct from the second, third, fourth, etc. sensing moieties. In other aspects, the first sensing moiety is the same as at least one of the second, third, fourth, etc. sensing moieties, or is the same as each of the second, third, fourth, etc. sensing moieties. In further aspects, the pore-subunit polypeptide is covalently linked to a plurality of sensing moieties, which may all be the same, all be different, or combinations of sensing moieties may be used. Exemplary combinations include the attachment of various oligosaccharides and/or oligonucleotides. Therefore, more than one analyte or physical parameter can be assayed at the same time.

Thus, where the pore-forming or pore-subunit polypeptide is P and certain distinct sensing moieties are $S_1$, $S_2$, $S_3$, etc., the invention includes modified polypeptides, pore assemblies, biosensors, arrays, kits and methods wherein the modified polypeptide is $P\text{-}S_1$, $P\text{-}S_2$, $P\text{-}S_3$, $P\text{-}S_1S_1$, $P\text{-}S_2S_2$, $P\text{-}S_3S_3$, $P\text{-}S_1S_1S_1$, $P\text{-}S_2S_2S_2$, $P\text{-}S_3S_3S_3$, $P\text{-}S_1S_2$, $P\text{-}S_2S_1$, $P\text{-}S_1S_3$, $P\text{-}S_3S_1$, $P\text{-}S_2S_3$, $P\text{-}S_3S_2$, $P\text{-}S_1S_2S_3$, $P\text{-}S_3S_2S_1$ and such like, with the same or different sensing moieties attached, and where different sensing moieties are used, in various orders of attachment. Those of ordinary skill in the art will understand that the same individual combinations are possible where the pore-forming or pore-subunit polypeptides are different, e.g., $P_1$, $P_2$, $P_3$, $P_4$, $P_5$, $P_6$ and $P_7$ and such like, and that any one or more of the same or different polypeptides may be combined with any one or more of the same or different attached sensing moieties, and that the modified polypeptides may be combined into pores in any operative combination.

Further aspects of the invention are kits, which comprise, generally in one or more suitable containers, a plurality of pore-forming or pore-subunit polypeptides sufficient to form a pore, wherein at least one of the pore-subunit polypeptides is a modified pore-subunit polypeptide of the invention, or a precursor thereof, i.e., a modified pore-subunit polypeptide comprising a pore-subunit polypeptide covalently linked to a sensing moiety, or a precursor thereof. Where the modified pore-subunit polypeptides are supplied as precursors, the materials for converting the precursor into a modified pore-subunit polypeptide of the invention are included in the kit, such as one or more sensing moieties and, optionally, one or more components for covalently linking the one or more sensing moieties to the pore-subunit polypeptides.

The present invention also provides oligomeric and polymeric pore assemblies comprising a number of pore-subunit polypeptides sufficient to form a pore, wherein at least one of the pore-subunit polypeptides is a modified pore-subunit polypeptide of the invention, i.e., a modified pore-subunit polypeptide comprising a pore-subunit polypeptide covalently linked to a sensing moiety.

In certain aspects of the invention, the pore assembly comprises at least 1, 2, 3, 4, 5, 6, 7, 8, 9, 10 or more modified pore-forming or pore-subunit polypeptides. Thus, in certain aspects, the pore assembly comprises a plurality of modified pore-subunit polypeptides. In yet other aspects, the pore assembly is comprised completely of modified pore-subunit polypeptides.

Irrespective of the number of modified pore-subunit polypeptides within the pore assembly, so long as there is at least one, the pore assemblies of the invention may comprise between about 1 and about 100 pore-subunit polypeptides.

The use of one pore-subunit polypeptide requires that the pore-subunit polypeptide form a pore by itself and be a modified pore-subunit polypeptide of the invention.

In certain aspects, the pore assemblies of the invention comprise 1, 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 101 or about 102 or more pore-subunit polypeptides.

In such pore assemblies, all, or substantially all, of the pore-subunit polypeptides may be modified pore-subunit polypeptides of the present invention. Alternatively, the modified pore-subunit polypeptides of the present invention may make up about 5%, about 10%, about 15%, about 20%, about 30%, about 40%, about 50%, about 60%, about 70%, about 80%, about 90% or about 95% or so of the pore-subunit polypeptides within the pore assembly.

Where the pore assemblies of the invention comprise two or more, or a plurality of the modified pore-subunit polypeptides of the invention, the modified pore-subunit polypeptides may each be linked to the same sensing moiety, or each be linked to distinct sensing moieties. The modified pore-subunit polypeptides may be linked to at least two distinct sensing moieties, up to and including being linked to as many distinct sensing moieties as modified pore-subunit polypeptides within the pore assembly.

In preferred embodiments, the pore assemblies comprise the amount of pore-subunit polypeptides that form in the natural environment. For example, the pore assemblies may comprise 3, 4, 5, 6, 7, 8, 9 or 10 or so pore-subunit polypeptides. Where the pore-subunit polypeptides and modified pore-subunit polypeptides are substantially all staphylococcal hemolysin polypeptides, such as staphylococcal alpha hemolysin polypeptides, the pore assemblies may preferably comprise 7 pore-subunit polypeptides, which may be include any number from 1 to 7 modified pore-subunit polypeptides of the invention. In other instances, the use of 3 polypeptides is particularly preferred, such as in certain porins that form pores as trimers.

Thus, the invention provides pore assemblies of the formula WTx-nMODn, wherein WT is an unmodified pore-subunit polypeptide, MOD is a modified pore-subunit polypeptide of the invention, n is an integer of 1 or greater than 1 and n is less than or equal to x, with x being an integer. That is, n is an integer of 1 or greater than 1 and x is an integer that is greater than or equal to n. Preferably, n and x are each integers from 1 to 100. Where x is equal to n, the pore assembly comprises only modified pore-subunit polypeptides of the invention.

Additionally, the present invention provides biosensor devices and arrays, digital biosensor devices, and arrays and integrated circuits thereof, comprising one or more of the modified pore-subunit polypeptides of the invention, preferably, in the form of one or more of the oligomeric and/or polymeric pore assemblies of the invention. That is, the biosensor devices comprise a number of pore-subunit polypeptides sufficient to form a pore, wherein at least one of the pore-subunit polypeptides is a modified pore-subunit polypeptide comprising a pore-subunit polypeptide covalently linked to at least a first sensing moiety.

In certain preferred embodiments, the biosensors, devices and arrays of the invention are fabricated to detect electrical current. The biosensor devices may detect a single channel current or may detect a current through two, more than two or a plurality of channels. In detecting electrical current, the devices of the invention are able to detect changes in ionic current flowing through a pore so that they are able, for example, to detect, quantitate and/or discriminate between components driven through the pore by an applied potential.

Biosensor arrays preferably comprise two or more of the oligomeric and/or polymeric pore assemblies of the invention, most preferably where the pore assemblies comprise modified pore-subunit polypeptides comprising distinct sensing moieties that sense distinct analytes or physical parameters. Such arrays provide for the simultaneous detection of multiple analytes or physical parameters. In the stochastic sensing of the present invention, each element does not need to be entirely specific for a given analyte, as a signature or "profile" is still generated that allows the detection, and optional quantification, of the given or more then one analyte(s).

Biosensors generally have three elements: a sensing moiety that either binds to or is bound by one or more target analytes, or responds to one or more physical parameters or properties; a transduction mechanism that signals the binding of the analyte(s) or the alteration of the sensing moiety in response to the physical parameter(s); and a means for, or a method of, measuring, and preferably processing, the transduction signal. Operative aspects of biosensors that may be combined for use in the present invention are described in published PCT patent application WO 99/05167, filed Jul. 24, 1998; U.S. provisional patent application 60/053,737, filed July 25, 1997; U.S. patent application Ser. No. 09/122,583, filed Jul. 24, 1998; and in U.S. Pat. Nos. 5,777,078, 5,817,771 and 5,824,776, each of which are specifically incorporated herein by reference in their entirety.

The sensing moieties of the invention are covalently linked to pore-forming polypeptides to give modified pore-forming polypeptides that self-assemble into pores. The transduction mechanisms that signal the binding of analytes and/or the alteration of the sensing moieties in response to physical parameters are adapted for use with the particular sensing moieties and detection means. For example, transduction mechanisms that signal the fractional occupancy of the sensing moiety by analytes and/or the physical and/or chemical state of sensing moiety under different conditions. Exemplary transduction mechanisms include materials flowing through the pore assemblies.

The biosensors of the present invention are thus useful in the detection of any analyte, component or physical parameter that contacts or impacts the measurable channel of the pore assembly. For use in single channel mode, an individual analyte is detected as it randomly, i.e., stochastically, binds to and releases from a single binding site. These events are detectable as modification or perturbations of the ion conductance in the single channel.

Preferably, the biosensor devices of the invention comprise means to detect the signal sensed by the at least a first sensing moiety of the modified pore-subunit polypeptide, oligomeric and/or polymeric pore assembly or assemblies. In certain preferred embodiments, the means is means to detect an electrical current or ion flux. In other embodiments, the detection means is means to detect signals based upon fluorescence or phosphorescence, or means to detect signals based upon atomic force microscopy. Means to detect an electromagnetic signal, such as a visible, ultraviolet, infrared, near-infrared or x-ray signal are also possible.

The biosensor devices of the invention may also comprise additional components, such as one, two or a plurality of signal amplification means and processing means, such as microprocessors and amplifiers. Sampling means may also be provided.

The present invention also provides various detection methods using one or more of the modified pore-subunit polypeptides, preferably, in the form of one or more of the oligomeric and/or polymeric pore assemblies or one or more of the biosensor devices of the invention. That is, the invention provides detection methods using at least a first of the oligomeric or polymeric pore assemblies or biosensor devices of the invention in which a signal, such as an electrical current, is detected through at least a first channel, a single channel or two or more channels.

Preferably, the signal, whether an electrical current or other signal, and whether detected through a single channel or two or more channels, is compared to a "control" signal measurement, such as a control current measurement; wherein a modulation or perturbation in signal, e.g., current, compared to an equivalent measurement in the control indicates the presence of the substance, event or change to be detected. In certain embodiments, the "control" signal measurement is actually measured in a "control sample", but it need not be. An advantageous feature of the invention is that parallel controls do not need to be run, i.e., the invention is self-calibrating.

The invention thus provides methods of detecting, and optionally quantifying, the presence of an analyte in a sample, comprising contacting the sample with one or more oligomeric and/or polymeric pore assemblies or biosensor devices of the invention, and detecting a signal or electrical current through at least a first channel, wherein a modulation in signal or current compared to a signal or current measurement in a control sample lacking the analyte indicates the presence of the analyte in the sample. The amount of the analyte in the sample may be readily quantitated by quantifying the signal or electrical current detected.

These methods comprise contacting the sample with one or more oligomeric and/or polymeric pore assemblies or biosensor devices of the invention, i.e., comprising a number of pore-subunit polypeptides sufficient to form a pore, wherein at least one of the pore-subunit polypeptides is a modified pore-subunit polypeptide comprising a pore-subunit polypeptide covalently linked to a sensing moiety, and detecting an electrical current through at least a first channel, wherein a modulation in current compared to a current measurement in a control sample lacking the analyte indicates the presence of the analyte in the sample.

An electrical current may be detected through a single channel. Such single channel detection in the digital mode provides a signature of the analyte, providing information on both the concentration of the analyte, as well as the identity of the analyte. In certain aspects of the invention, once the pore assembly has been validated, there is no need to run a control to determine the analyte signature, thus creating a "self-calibrating" sensor. As such, the "comparison" step can be an inherent feature that is not re-executed in real time alongside every analyte measurement. Such digital monitoring can also be used in single molecule detection.

An electrical current may also be detected through at least two channels, wherein a modulation in current compared to a current measurement in a control sample lacking the analyte indicates the presence of the analyte in the sample. In general, using two or more, or macroscopic, channels provides information in the change of the pore environment, without providing a specific analyte signature.

In addition to single and multiple channel detection, a number of other detection methods are contemplated for use in the present invention, including, but not limited to, fluorescence, phosphorescence, and atomic force microscopy. Such signals may be detected by the detection means exemplified above and known those of ordinary skill in the art in light of the present disclosure.

The present invention also provides methods of detecting the presence of an unknown analyte in a sample, comprising contacting the sample with one or more oligomeric and/or polymeric pore assemblies or biosensor devices of the invention, and detecting a signal or electrical current through at least a first channel to determine a sample current signature, and comparing the sample current signature to a standard current signature of a known analyte, wherein a concurrence of the sample current signature and the standard current signature indicates the identity of the unknown analyte in the sample.

Such methods comprise contacting the sample with one or more oligomeric pore assemblies comprising a number of pore-subunit polypeptides sufficient to form a pore, wherein at least one of the pore-subunit polypeptides is a modified pore-subunit polypeptide comprising a pore-subunit polypeptide covalently linked to a sensing moiety, detecting an electrical current through a single channel to determine a sample current signature, and comparing the sample current signature to a standard current signature of a known analyte, wherein a concurrence of the sample current signature and the standard current signature indicates the identity of the unknown analyte in the sample.

These methods further contacting the sample with one or more oligomeric pore assemblies comprising a number of pore-subunit polypeptides sufficient to form a pore, wherein at least one of the pore-subunit polypeptides is a modified pore-subunit polypeptide comprising a pore-subunit polypeptide covalently linked to a sensing moiety, detecting an electrical current through at least two channels to determine a sample current signature, and comparing the sample current signature to a standard current signature of a known analyte, wherein a concurrence of the sample current signature and the standard current signature indicates the identity of the unknown analyte in the sample.

Furthermore, the present invention provides methods of detecting a change in the type or amount of a biological or chemical constituent in a sample, comprising the steps of contacting the sample with one or more oligomeric and/or polymeric pore assemblies or biosensor devices of the invention at a first time point; determining a first sample current signature by detection of an electrical current through at least a first channel, a single channel or through two channels; contacting the sample with one or more oligomeric and/or polymeric pore assemblies or biosensor devices of the invention at a second time point; determining a second sample current signature by detection of an electrical current through at least a first channel, a single channel or through two channels; and comparing the first sample current signature to the second sample current signature, wherein a difference between the first sample current signature and the second sample current signature is indicative of a change in the type or amount of a biological or chemical constituent in the sample.

In all methods where measurements are made at least at a first and second time point, the time points may be two or more time points at any instance of operation in a continuous flow mode.

Such methods comprise contacting the sample with one or more oligomeric pore assemblies comprising a number of pore-subunit polypeptides sufficient to form a pore, wherein at least one of the pore-subunit polypeptides is a modified pore-subunit polypeptide comprising a pore-subunit polypeptide covalently linked to a sensing moiety at a first time point; determining a first sample current signature by detection of an electrical current through at least a first channel, a single channel or through two channels; contacting the sample with one or more oligomeric pore assemblies comprising a number of pore-subunit polypeptides sufficient to form a pore, wherein at least one of the pore-subunit polypeptides is a modified pore-subunit polypeptide comprising a pore-subunit polypeptide covalently linked to a sensing moiety at a second time point; determining a second sample current signature by detection of an electrical current through at least a first channel, a single channel or through two channels; and comparing the first sample current signature to the second sample current signature, wherein a difference between the first sample current signature and the second sample current signature is indicative of a change in the type or amount of a biological or chemical constituent in the sample.

In embodiments where the attached polymer is an oligonucleotide or polynucleotide, such as single-stranded DNA or RNA, the invention further provides methods of nucleic acid detection and analysis. For example, the invention provides methods of detecting defined nucleic acid sequences using one or more oligomeric and/or polymeric pore assemblies or biosensor devices of the invention in which the attached sensing moiety is itself a nucleic acid. A range of such sequence detection methods is possible. These include, but are not limited to, methods of detecting the presence of a nucleic acid of unknown sequence in a sample.

Such methods generally comprise contacting the sample with one or more oligomeric and/or polymeric pore assemblies or biosensor devices of the invention, in which at least a first pore-forming or pore-subunit polypeptide is covalently linked to at least a first nucleic acid that acts as a sensing moiety, preferably, at least a first nucleic acid of known sequence that acts as a sensing moiety; detecting a signal or electrical current through at least a first channel, a single channel or two or more channels, to determine a sample current signature; and comparing the sample current signature to a standard current signature of a nucleic acid of known sequence, wherein a concurrence of the sample current signature and the standard current signature indicates the identity of the nucleic acid of unknown sequence in the sample.

Preferably, the at least a first nucleic acid that acts as a sensing moiety has a known sequence; and the methods are used to discriminate between nucleic acids in the sample of exactly the complementary sequence, substantially the complementary sequence and those nucleic acids that do not have exactly or substantially the complementary sequence.

The nucleic acids are preferably on the order of between about 6 and about 50 nucleotides in length. The sequences to be detected are limitless, as exemplified by detecting sequence variations of diagnostic and/or prognostic significance in human, veterinary, agricultural, environmental and/or microbiological significance.

Further embodiments of using pores, pore assemblies and biosensors with covalently attached nucleic acid elements are in sequencing nucleic acids. In these aspects of the invention, the at least a first pore-forming or pore-subunit polypeptide of the invention may be covalently linked to at least a first nucleic acid of known or unknown sequence. Those with known attached sequences may be used as described above to specifically detect, and thus sequence, complementary nucleic acids.

Accordingly, multiple copies of nucleic acids with sequences from a given molecule may be arrayed in a pore assembly or biosensor. The plurality of oligonucleotides arrayed in the pore assembly or biosensor may each have a substantially distinct sequence from a given molecule, such as, e.g., a pathogen or oncogene, thus allowing detection of hybridizing sequences. The plurality of oligonucleotides arrayed as such may also have sequences from a parent molecule that overlap by one nucleotide residue per oligonucleotide, such that an overlapping array of pathogen- or oncogene-derived sequences are presented.

Pores, pore assemblies and biosensors in which the polypeptides of the invention are covalently linked to at least a first nucleic acid of unknown or partially unknown sequence can also be readily used in sequencing. In such embodiments, the pores are interrogated in sequence with candidate oligonucleotides, allowing those that hybridize to be identified in sequential format.

Arrays of pores, pore assemblies and biosensors with covalently attached nucleic acids of known, unknown or partially known and unknown sequences may thus be used in essentially the same manner as the sequence detection chips with immobilized nucleic acids available in the art. Although the biosensors of the present invention provide the various improved features described herein and apparent in the practice of the invention, the execution of the nucleic acid binding steps and assimilation and analysis of the information generated, preferably using computer-based algorithms, has parallels in the "sequencing chip" technology. The following patents and patent applications are each incorporated herein by reference for purposes of even further exemplifying the use of immobilized nucleic acids in detection and sequencing: WO 95/09248: U.S. Pat. Nos. 5,202,231; 5,695,940; 5,525,464; 5,667,972; 5,202,231; 5,492,806; WO 99/09217; and WO 98/31836.

Additionally, the present invention provides methods of detecting, and optionally quantifying, a change in the physical environment of a sample, comprising contacting the sample with one or more oligomeric and/or polymeric pore assemblies or biosensor devices of the invention at a first time point; determining a first sample current signature by detection of an electrical current through at least a first channel, a single channel or through two channels; contacting the sample with one or more oligomeric and/or polymeric pore assemblies or biosensor devices of the invention at a second time point; determining a second sample current signature by detection of an electrical current through at least a first channel, a single channel or through two channels; and comparing the first sample current signature to the second sample current signature, wherein a difference between the first sample current signature and the second sample current signature is indicative of a change in the physical environment of the sample.

The change in the physical environment may be readily quantitated by quantifying the signal or electrical current detected. The change(s) in the physical environment may also be determined as an ongoing process, i.e., in a continuous flow mode. That is, the first and second samples, pore assemblies and current signatures do not need to be physically separate, only temporally distinct.

These methods of the invention comprise the steps of contacting the sample with one or more oligomeric pore assemblies comprising a number of pore-subunit polypeptides sufficient to form a pore, wherein at least one of the pore-subunit polypeptides is a modified pore-subunit polypeptide comprising a pore-subunit polypeptide covalently linked to a sensing moiety at a first time point; determining a first sample current signature by detection of an electrical current through at least a first channel, a single channel or through two channels, contacting the sample with one or more oligomeric pore assemblies comprising a number of pore-subunit polypeptides sufficient to form a pore, wherein at least one of the pore-subunit polypeptides is a modified pore-subunit polypeptide comprising a pore-subunit polypeptide covalently linked to a sensing moiety at a second time point; determining a second sample current signature by detection of an electrical current through at least a first channel, a single channel or through two channels; and comparing the first sample current signature to the second sample current signature, wherein a difference between the first sample current signature and the second sample current signature is indicative of a change in the physical environment of the sample.

BRIEF DESCRIPTION OF THE DRAWING

The following drawings form part of the present specification and are included to further demonstrate certain aspects of the present invention. The invention may be better understood by reference to one or more of these drawings in combination with the detailed description of illustrative embodiments presented herein. All drawings in U.S. provisional application Serial No.60/182,097, filed Feb. 11, 2000, are specifically incorporated herein by reference without disclaimer.

FIG. 2A, FIG. 2B, FIG. 2C and FIG. 2D. FIG. 2A and FIG. 2B. A representative current trace and semi-logarithmic amplitude histogram for a single channel current from $H_6S106C$-PEG5K$_1$. The current was recorded at +100 mV under symmetrical buffer conditions: 300 mM KCl, 5 mM Tris-HCl (pH=7.00), 100 μM EDTA. The bilayer lipid was 1,2-diphytanoyl-sn-glycerophosphocholine. Protein was added to the cis chamber, which was at ground. A positive potential indicates a higher potential in the trans chamber and a positive current is one in which cations flow from the trans to the cis chamber. The current was low-pass filtered at 100 Hz and sampled at 10 kHz. An expanded view of a high amplitude subsrtate (the last spike in the trace) is shown filtered at 3 kHz. d, low amplitude subconductance state; s, short-lived spike. FIG. 2C and FIG. 2D. Signal from the same channel after treatment with 12 mM DTT in the cis chamber, filtered at 100 Hz.

FIG. 3A. Representative single channel current trace exhibiting short-lived high-amplitude spike-like partial closures. FIG. 3B. Threshold histogram from an extended period (1 min) of the current trace excerpted in FIG. 3A. The signal was filtered at 8 kHz and sampled at 200 kHz. The threshold was set at 15 pA. Only the signal 0.5 ms before and after each spike was recorded and used in the histogram. Hence the peak at ~10 pA, arising from the spikes, is exaggerated.

FIG. 4A, FIG. 4B, FIG. 4C, FIG. 4D, FIG. 4E-1, FIG. 4E-2, FIG. 4E-3, FIG. 4F, FIG. 4G and FIG. 4H. Response of $H_6106C$-PEG-biotin, to WT and W120A streptavidins. Single-channel current recordings. In FIG. 4A–FIG. 4D, the bars show biotin capture events. The streptavidins were added before the start of each trace. FIG. 4A. WT streptavidin (12 nM) added to the cis chamber abolishes the high-amplitude spikes. FIG. 4B. WT streptavidin (12 nM) added to the trans chamber leads to a permanent partial channel blockade closely similar in amplitude to the amplitude of the spikes. FIG. 4C. W120A streptavidin (7.25 nM) added to the cis chamber leads to transient disappearances of the high-amplitude spikes, but does not alter the underlying current. FIG. 4D. W120A streptavidin (7.25 nM) added to the trans chamber produces transient partial channel blockades closely similar in amplitude to the amplitude of the spikes. FIG. 4E-1, FIG. 4E-2 and FIG. 4E-3. The inter-event interval ($\tau_{on}$) decreases with increasing W120A streptavidin. FIG. 4F. Plot of $1/\tau_{on}$ versus W120A streptavidin concentration. Data from a single typical study are plotted in FIG. 4E-1, FIG. 4E-2, FIG. 4E-3 and FIG. 4F as least-squares fits. In FIG. 4G and FIG. 4H, the thick bars show trans biotin capture events and the thin bars cis events. The streptavidins were added before the start of each trace. FIG. 4G. W120A streptavidin (7.25 nM) was added to the cis chamber and WT streptavidin (71.7 nM) to the trans chamber. Cis capture of biotin by W120A streptavidin produces transient disappearances of the spikes. By contrast, trans capture by WT streptavidin resulted in a permanent blockade. FIG. 4H. W120A streptavidin (7.25 nM) was added to the cis chamber and WT120A streptavidin (29 nM) was added to the trans chamber producing transient events by capture on both the cis and trans sides.

FIG. 5A. mAb (5.8 nM) was added to the trans chamber. A single capture event is shown. FIG. 5B. mAb (29 nM) was added to the trans chamber with W120A streptavidin (7.25 nM) in the cis chamber. Both cis and trans capture events are shown.

FIG. 6A and FIG. 6B show the preparation of the αHL pore $H_6(17C$-oligo-A)$_1$. FIG. 6A. Autoradiogram of an SDS-polyacrylamide gel after electrophoresis of a mixture of unmodified αHL monomers, H, and 17C-oligo-A-D4 monomers cross-linked to oligo-A (5'-CATTCACC-3'; SEQ ID NO: 1) through a disulfide bond, in the absence (lane 1) and presence (lane 2) of the reducing agent DTT. The DNA-modification causes 17C-oligo-A-D4 to migrate more slowly (compare lane 1, 17C-oligo-A-D4 with lane 2, 17C-D4). 17C-D4 (lane 2) migrates more slowly than H by virtue of a C-terminal extension of four aspartates (D4-tag). FIG. 6B. Autoradiogram of an SDS-polyacrylamide gel containing heteroheptamers formed by the assembly of a mixture of H and 17C-oligo-A-D4 monomers. Heptamers $H_7$, $H_6$(17C-oligo-A)$_1$ and $H_5$(17C-oligo-A)$_2$ migrate in different gel bands due to a shift caused by the D4-tag in the 17C-oligo-A-D4 subunits. The modification with DNA does not change the electrophoretic mobility of modified heptamers. The size of two molecular weight markers is indicated.

FIG. 7A-1, FIG. 7A-2, FIG. 7B-1, FIG. 7B-2, FIG. 7C-1 and FIG. 7C-2. An αHL pore modified with a single DNA-oligonucleotide responds to individual binding events of oligonucleotides of complementary sequence (FIG. 7A-2, FIG. 7B-2 and FIG. 7C-2). FIG. 7A-1. Representative single channel current trace of $H_6$(17C-oligo-A), at a transmembrane potential of +100 mV relative to the cis side of the bilayer in 2 M KCl, 12 mM $MgCl_2$, 5 mM Tris-HCl, pH 7.4. FIG. 7B-1. Representative trace of the same channel as in FIG. 7A-1 in the presence of 67 nM oligo-B (3'-GTAAGTGG-5'; SEQ ID NO:2) in the chamber at the cis side of the protein. Negative current deflections (b) represent individual binding events of oligo-B to the tethered oligo-A. The short downward spike (s) in the trace is a translocation event of oligo-B that did not bind to the tethered oligonucleotide. FIG. 7C-1. Trace of the same channel as in FIG. 7A-1 and FIG. 7B-1 with 67 nM oligo-B and 3.3 μM oligo-A in the cis chamber. Excess oligo-A hybridizes to oligo-B and thereby competes for the binding of oligo-B to the tethered oligonucleotide. The short downward spikes in the trace are translocation events of excess oligo-A molecules through the pore.

FIG. 8A. Definition of event lifetime $\tau_{off}$ and event amplitude $I_E$. FIG. 8B. An event diagram shows the event lifetime $\tau_{off}$ and event amplitude $I_E$ for a single channel current recording of 3 min with 200 nM oligo-B in the cis chamber. Each point in the diagram represents an individual binding event of oligo-B to the tethered oligo-A in $H_6$(17C-oligo-A)I.

DESCRIPTION OF ILLUSTRATIVE EMBODIMENTS

Staphylococcal α-hemolysin (αHL) has been a useful model system with which to test new approaches for engineering membrane proteins and indeed proteins in general.

Figure 1:
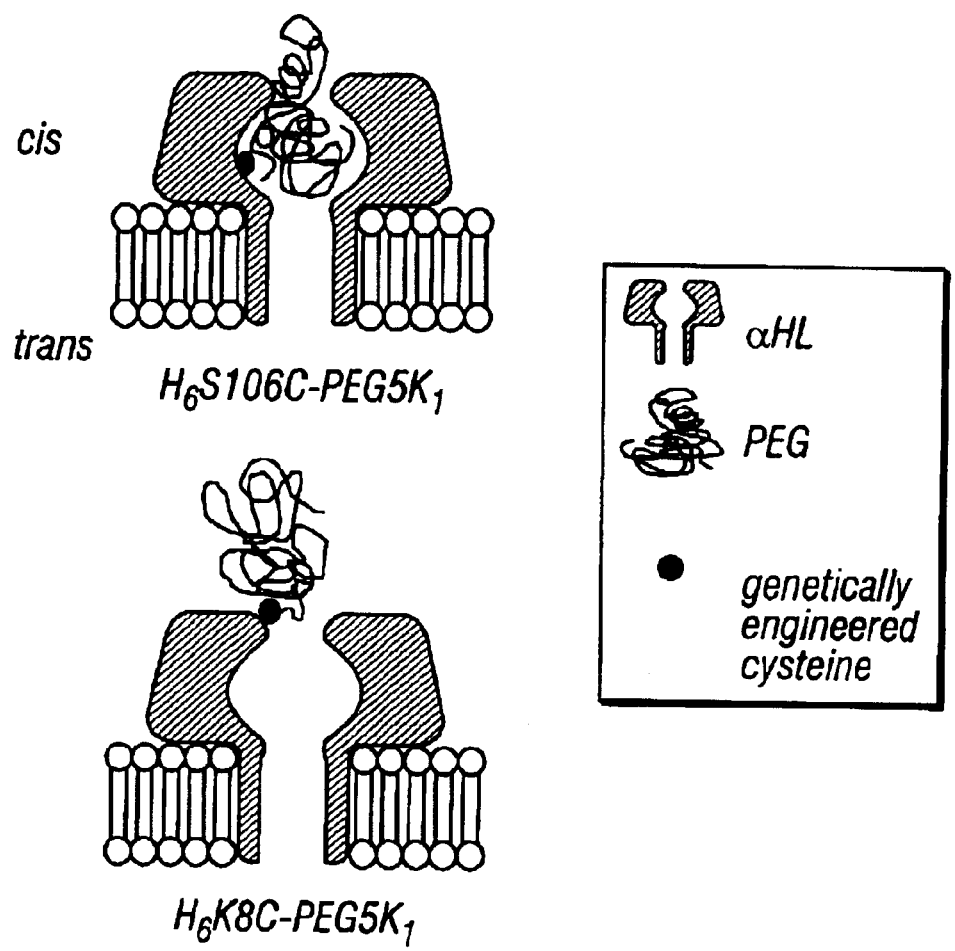
FIG. 1. Schematics of $H_6S106C$-PEG5K$_1$ and $H_6K8C$-PEG5K$_1$, shown as sagittal sections. In each engineered pore, only one of the seven subunits is modified. In this work, the mutant K8A was used as the unmodified αHL subunit (H), so that the net charge at the cis channel entrance would not be altered in heteromers containing K8C-PEG5K.

The α-Hemolysin toxin is secreted by *Staphylococcus aureus* as a monomeric polypeptide of 293 amino acids. The monomer forms heptameric, mushroom-shaped pores of known three-dimensional structure in lipid bilayers (Song et al., 1996; Gouaux, 1998). The opening of the channel on the cis side of the bilayer measures 29 A in diameter and broadens into a cavity ~41 Å across (FIG. 1).

The αHL pore allows the passage of molecules of up to ~2000 Da across the bilayer (Fussle et al., 1981; Krasilnikov et al., 1992; Bezrukov et al., 1996; Bezrukov et al., 1997) and is only weakly selective for the charge of transported ions (Menestrina, 1986). Besides being the object of a variety of studies using mutagenesis (Walker et al., 1993; Walker and Bayley, 1995a; Braha et al., 1997; Cheley et al., 1999), αHL has been subjected to protein engineering by targeted chemical modification. These studies include the attachment of photocleavable protecting groups to block assembly (Chang et al., 1995), the restoration of activity to an inactive mutant by site-specific alkylation (Walker and Bayley, 1995b), and the formation of channel blocker sites with non-covalent molecular adapters (Gu et al., 1999).

The present invention describes new, targeted modifications that are introduced, including the attachment of a synthetic polymer chain, which may be attached at the surface or within the lumen of the pore. Single channel electrical recording has been used to observe current fluctuations associated with the attachment of the polymer, a 3000 or 5000 Da polyethylene glycol (PEG) molecule.

In addition to the protein engineering, the present invention has applications in at least two areas: single molecule detection and the development of biosensors. The examination and manipulation of individual molecules is a thriving area of research. Single molecule detection methods, which include electrical recording (Hladky and Haydon, 1970; Sakmann and Neher, 1995), optical spectroscopy (Moerner and Orrit, 1999; Weiss, 1999) and force measurements (Mehta et al., 1999), can provide structural and functional information that is often difficult or impossible to obtain by conventional techniques, which measure the properties of large ensembles of molecules. Recent accomplishments include observations of the movement of individual atoms and small molecules (Gimzewski and Joachim, 1999), the movement of linear and rotary motor proteins (Mehta et al., 1999), the turnover of individual enzymes (Xie and Lu, 1999) and the unfolding and refolding of proteins (Mehta et al., 1999).

In the area of biosensors, significant progress has been made in developing protein channels and pores as sensor elements (Ziegler and Gopel, 1998; Bayley, 1999; Hoffman, 1995; Urry, 1998; Hubbel, 1999). According to this concept, analyte molecules modulate the ionic current passing through the pores under a transmembrane potential. For example, binding sites can be engineered into pores expressly for capturing analyte molecules, which act as partial channel blockers. Stochastic sensing, which uses currents from single pores, is an especially attractive prospect (Braha et al., 1997; Gu et al., 1999). The approach yields both the concentration and identity of an analyte, the latter from its distinctive current signature. By using αHL as a stochastic sensing element, the inventors have succeeded in detecting divalent metal ions (Braha et al., 1997) and a variety of organic molecules (Gu et al., 1999). The present invention represents a major step towards using responsive polymers for stochastic sensing.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

A Protein Pore With a Single Polymer Chain Tethered Within the Lumen

The present example describes a transmembrane protein pore with a single 5000 Da polyethylene glycol (PEG) molecule attached covalently within the channel lumen has been constructed from seven staphylococcal α-hemolysin subunits. The modified heptamer is stable and can be purified by electrophoresis in sodium dodecyl sulfate, without dissociation of the subunits. The properties of the modified pore were studied by single channel current recording. The PEG molecule reduces the mean conductance of the pore by 18%, as would be predicted from the effects of PEG on the conductivity of bulk electrolytes. The recordings also reveal a variety of low amplitude current fluctuations on a timescale of seconds, which are tentatively ascribed to the reorganization of the PEG molecule within the channel lumen and associated movements of the polypeptide chain. Another class of events, comprising uniform high-amplitude negative fluctuations in current with durations of milliseconds, is ascribed to motions of the PEG molecule into one of the channel entrances, thereby producing more extensive channel block. When instead a 3000 Da PEG is attached within the channel lumen, the single channel properties are changed in keeping with the lower mass of the polymer. For example, the high-amplitude fluctuations occur more frequently and are of shorter duration suggesting that the 3000 Da PEG is more mobile than the 5000 Da chain. The approach taken here is useful for the indirect monitoring of polymer dynamics at the single molecule level. By using polymers that respond to analytes, biosensors can be made from the covalently modified pores.

A. Materials and Methods

1. Proteins

The mutant αHL S106C gene was obtained by cassette mutagenesis of the semisynthetic gene αHL-RL210. S106C also contains the mutation Lys-8->Ala, and four conservative replacements: Val-124->Leu, Gly-130->Ser, Asn-139->Gln, and Ile-142->Leu. These changes, which were introduced to prevent adventitious proteolysis (Walker and Bayley, 1994) and to facilitate cassette mutagenesis (Cheley et al., 1999), do not alter the electrical properties of the pore (Cheley et al., 1999). The K8A and K8C constructs have already been described (Walker and Bayley, 1995a; Walker and Bayley, 1994). $^{35}$S-labeled αHL polypeptides K8A, K8C and S106C were obtained by expression in vitro (Walker et al., 1992a). To increase the yield of protein, unlabeled methionine was included in the translation mix (Cheley et al., 1999; Walker et al., 1992b). K8A was used as the unmodified αHL subunit (H) in heteroheptameric pores. Therefore, when a PEG-modified K8C subunit is included in the heptamer, the charge at position 8 is not altered as it would be if the wild-type protein were used.

2. Chemical Modification of Single-Cysteine Mutants

K8C or S106C monomers were diluted 6-fold from the translation mix into a buffer containing 10 mM MOPS-NaOH, pH 7.4, 150 mM NaCl, 0.5 mM EDTA and reduced with 0.5 mM DTT for 10 min, before modification with 10 mM monomethoxy-PEG5000-o-pyridyldisulfide (MePEG5K-OPSS, Shearwater Polymers) for 20 min at 25° C. Treatment with MePEG3K-OPSS was performed in the same way.

3. PEG-Modified Heteroheptameric Pores

The modified K8C or S106C monomers were mixed with unmodified K8A αHL monomers (H) in various initial ratios and the mixed subunits were allowed to assemble on rabbit erythrocyte membranes (Walker et al., 1992a). To analyze which heteromers had been formed with PEG5000-modified subunits, the membranes were recovered by centrifugation, dissolved in gel loading buffer and loaded, without heating, onto a 6% SDS-polyacrylamide gel (5-cm long, 0.75 mm thick, Miniprotean II, Biorad). To determine subunit ratios, the samples were heated and analyzed in a 10% SDS-polyacrylamide gel. The dried gels were subjected to phosphorimager or autoradiographic analysis.

To prepare the heteromers $H_6S$ 106C-PEG5K$_1$ and $H_6$K8C-PEG5K$_1$ for bilayer recording, subunits were assembled in the ratios: H: S106C-PEG5K, 3: 4; H: K8C-PEG5K, 6:1. Samples corresponding to a total of 12 µl of translation mix per lane were loaded, without heating, onto 6% SDS-polyacrylamide gels (35 cm long, 1.5 mm thick), which were run for 18 h at 150V. The unfixed gels were vacuum dried at 50° C. onto Whatman 3mM paper and the protein bands located by autoradiography. The desired bands were cut from the gel and rehydrated in water (300 µl per lane). After removal of the paper, the gel was crushed in the water and the mixture was left to stand for 10 h at 4° C. A solution of PEG-modified heptamers was then obtained by removal of the acrylamide with a cellulose acetate filter (0.2 µm diameter, Rainin, Woburn, Mass.). PEG3000 produced no gel shift in heteroheptamers modified at position 106. Therefore, to make $H_6$S106C-PEG3K$_1$, unmodified subunits (H) and S106-PEG3K were assembled together in a ratio of 4:3. After preparative SDS-polyacrylamide gel electrophoresis, as described above, the major band contained 40% $H_6$S106C-PEG3K, and ~60% $H_7$, as deduced from the subunit ratio determined by analytical SDS-polyacrylamide gel electrophoresis and by the results of single channel recording.

4. Planar Bilayer Recordings

Planar lipid membrane recordings were carried out at 24±1° C. (Braha et al., 1997; Gu et al., 1999; Montal and Mueller, 1972). The cis and trans chambers, each of 2 ml, were separated by a 25-µm-thick Teflon septum (Goodfellow Corporation, Malvern, Pa.). An aperture in the septum (~150-µm diameter) was pretreated with 10% (v/v) hexadecane (Aldrich Chemical Co., Milwaukee, Wis.) in n-pentane (Burdick & Jackson, Muskegon, Mich.). The electrolyte in both chambers was 300 mM KCl, 5 mM Tris-HCl, pH 7.0, containing 100 µM EDTA. A bilayer membrane was formed (Montal and Mueller, 1972) with 1,2-diphytanoyl-sn-glycerophosphocholine (Avanti Polar Lipids, Alabaster, Ala.). αHL pores were introduced by adding gel-purified heptamers (1 to 6 µl) to the cis chamber, to give a final protein concentration of 0.05–0.3 ng/ml. The cis solution was stirred for 5–30 min until a single pore inserted (8–10 pA step at −40 mV).

Currents were recorded by using a patch clamp amplifier (Axopatch 200B, Axon Instruments, Foster City, Calif.) connected to the chambers by Ag/AgCl electrodes, and monitored with an oscilloscope (Model TAS250, Tektronix, Heenveen, Netherlands). The cis chamber was grounded and a negative current (downward deflection) represents positive charge moving from the cis to trans side. A Pentium PC equipped with a DigiData 1200 A/D converter (Axon Instruments, Foster City, Calif.) and a strip chart recorder (BD112, Kipp & Zonen, Bohemia, N.Y.) were used for data acquisition. For the most of the studies, the current traces were low-pass filtered with a built-in 4-pole Bessel filter at a frequency of 5 kHz and stored by using a digital audio tape recorder (DAS-75, Dagan Corporation, Minneapolis, Minn.). For computer analysis, the data were further filtered with a 8-pole Bessel filter at frequencies in the range 100–3000 Hz and sampled at 10 kHz. For display and statistical analysis, the FETCHAN and pSTAT programs were used, both from the software package pCLAMP7 (Axon Instruments) and Origin (Microcal Software, Northampton, Mass.). In the case of $H_6S106C$-$PEG3000_1$, a different protocol was used to allow the examination of rapid events. The signal, filtered at 10 kHz, was recorded on digital audio tape. For analysis, the signal was filtered at 7 kHz with a low-pass Bessel filter and sampled at 333 kHz for computer acquisition using a threshold protocol in the CLAMPEX program from pCLAMP7.

Current amplitudes and life-times of the various conductance states are given as mean values (±s.d.). The value of "n" denotes the number of studies analyzed or, when indicated, the number of events examined.

B. Results

1. Engineering an αHL Pore With a Single PEG Molecule Tethered Within the Central Cavity In previous work, the inventors modified the lumen of the heptameric αHL pore by direct genetic engineering (Braha et al., 1997) and by non-covalent modification with molecular adapters (Gu et al., 1999). A principal goal has been to create protein pores that respond to various analytes and can thus be employed as components of biosensors, especially stochastic sensors in which single molecule detection is used. The inventors reasoned that an additional way to modify the interior of the protein would be by the covalent attachment of responsive molecules. Responsive polymers attached at specific sites in proteins have demonstrated potential. They have, for example, been used to modulate the affinity of streptavidin for biotin (Stayton et al., 1995; Ding et al., 1999).

To assemble an exemplary structure with an internal polymer, a 5000 Da PEG molecule was placed within (or largely within) the central cavity of the cap domain of the αHL pore. The calculated volume of PEG5000 based on the experimental hydrated radius (Krasilnikov et al., 1992; Scherrer and Gerhardt, 1971) is comparable to the volume of the cavity, which is 36,000 Å$^3$, assuming a sphere of diameter 41 Å. The Flory dimension (RF) of PEG5000 of 60 Å ($RF=aN^{06}$, where N, number of polymer repeat units; a, effective repeat length (3.5 Å)) (Doi, 1996), which has been variously interpreted as a radius or diameter (Kenworthy et al., 1995; Rex et al., 1998), gives a larger volume for PEG5000, but this may be unrealistic (Rex et al., 1998).

2. Heptamers Containing up to Seven PEG Molecules Can be Made by Derivatization at an External Site on the αHL Pore The PEG conjugation chemistry and a means to analyze the assembly of derivatized subunits were tested with the αHL single-cysteine mutant K8C. In this case, the PEG chains would end up located near the surface of the heptamer, at the cis mouth, and therefore be unlikely to interfere with assembly (FIG. 1) (Walker et al., 1995; Olson et al., 1999). $^{35}$S-labeled K8C polypeptides were obtained by expression in vitro (Walker et al., 1992a) and modified with monomethoxy-PEG5000-o-pyridyldisulfide (MePEG5K-OPSS). The PEG is attached to the protein through a disulfide bond that is readily cleaved with dithiothreitol (DTT). This was shown by extracting protein from an SDS-polyacrylamide gel band generated with a low fraction of S106C-PEG5K subunits (band a), heating to 95° C. for 5 min and separating in a second SDS-polyacrylamide gel. The bands were quantified by phosphorimager analysis. Analyzing lanes of heated band a ($H_6S106C$-$PEG5K_x$); heated and DTT-treated band a ($H_6S106C$-$PEG5K_1$); PEG-modified S106C monomer before heptamerization; and PEG-modified S106C monomer after DTT treatment gave rise to the present finding.

Analysis of H/K8C-PEG5K heteroheptamers by SDS-polyacrylamide gel electrophoresis and autoradiography revealed seven bands, a–g. The subunits were $^{35}$S-labeled during in vitro expression. K8C and S106C were reduced with 0.5 mM DTT and reacted with 10 mM MePEG5K-OPSS for 20 min at 25° C. The modified K8C polypeptides were mixed with unmodified $^{35}$S-labeled αHL monomers in all initial ratios between 0:7 and 7:0 the mixed subunits were allowed to assemble on rabbit erythrocyte membranes (Walker et al., 1992a). Following heptamerization on the erythrocyte membranes, autoradiograms were obtained. The number of PEG-modified subunits present in the heptamers in each band are: K8C a, 1; b, 0 and 2; c, 3; d, 4; e, 5; f, 6; g, 7; S106C a, 1 and 2; b, 0.

The protein in each band was eluted and heated to dissociate the subunits. Further electrophoresis revealed the ratio of subunits in each band, which showed that all eight possible combinations (Braha et al., 1997) of unmodified αHL (H) and K8C-PEG5K subunits had been formed (both $H_7$ and $H_5K8C$-$PEG5K_2$ are in band b). Interestingly, the electrophoretic mobility of heptamers containing a single PEG5000 molecule was increased (band a), while the mobilities of heptamers containing three or more attached PEG5000s (bands c–g) were decreased. Heptamers with two to five PEGs exist in more than one form: the outcome of permutation about the central seven-fold axis (Braha et al., 1997). Bands c and d were distinctly broadened, most likely reflecting an incomplete separation of the five permutations each of $H_4K8C$-$PEG5K_3$ and $H_3K8C$-$PEG5K_4$. These studies show that heptamers containing PEG5000 in an external location can be assembled and all eight combinations of subunits can be identified by analytical SDS-polyacrylamide gel electrophoresis.

3. A Single PEG Chain Can be Attached at a Point Within the Central Cavity of the αHL Pore The same approach was used to make heptamers containing PEG5000 attached covalently to a cysteine residue within the large central cavity (position 106 in the polypeptide chain). Modified S106C monomers were mixed with unmodified αHL monomers (H) and allowed to assemble on rabbit erythrocyte membranes (Walker et al., 1992a). By contrast with the results with K8C-PEG5K, the analysis of H/S106C-PEG5K heteroheptamers revealed only two major bands, suggesting that the formation of SDS-resistant heptamers containing several modified S106C subunits is disfavored due to crowding of the PEG chains within the central cavity. The measured ratio of unaltered αHL (H) to S106C-PEG5K subunits in band a was 5.9:1, and therefore the oligomer in the band must contain six unmodified subunits (H) and one S106-PEG5K subunit, namely $H_6S106C$-$PEG5K_1$. At high S106C-PEG5K:H ratios in the assembly mix, a faint band was seen above band a and may represent $H_5S106C$-$PEG5K_2$.

This study shows that $H_6S106C$-$PEG5K_1$ can be formed and that it is stable as a heptamer at room temperature in the denaturing detergent SDS. Therefore, the cavity might be large enough to contain a PEG5000 molecule. Any hydration pressure that develops in packing the PEG internally would have to be insufficient to dissociate the heptamer. Alternatively, unfavorable interactions would be reduced if part of the PEG chain were extruded through the cis or trans entrance. Studies with PEG3000 support the latter interpretation. The electrophoretic mobility of $H_6S106C$-PEG3$K_1$ is the same as that of the unmodified heptamer ($H_7$), suggesting that the hydrodynamic properties of the heptamer are unaltered and the PEG3000 chain is largely contained within the cavity. By contrast, the altered electrophoretic mobility of $H_6S106C$-PEG5$K_1$ suggests that part of the PEG5000 chain is exposed to solvent.

4. Ionic Current Through Individual PEG-Modified αHL Pores

The cavity in the αHL pore lies on the conductive pathway and so the incorporation of a PEG molecule at position 106 would be expected to alter the current that flows through the pore in response to an applied potential. This was tested by performing single channel current measurements on $H_6S106C$-PEG5K, eluted from preparative gels (Braha et al., 1997). The control homoheptamer ($H_7$) exhibits a uniform unitary conductance state (Table 1; Braha et al., 1997; Cheley et al., 1999; Gu et al., 1999).

By contrast, the PEG-modified αHL pore showed dynamic gating behaviors centered around a main conductance state of diminished amplitude compared with $H_7$ (FIG. 2A and FIG. 2B, Table 1). The mean of the main peaks in the conductance histograms for $H_6$S 106C-PEG5$K_1$ was 221±9 pS (n=7) at +100 mV, in symmetric 300 mM KCl, 5 mM Tris-HCl (pH 7.00), 100 μM EDTA, a reduction of 18% over the value for $H_7$ (Table 1). Two distinct subconductance behaviors were observed: relatively long-lived low amplitude fluctuations (mean life-time, 14.5±1.7 s, n=27 events) and short-lived higher amplitude negative spikes (mean life-time, 13.7±2.2 ms, n=87 events; frequency of occurrence 0.20±0.02 s-1). Typically there were three to five low amplitude states separated by Δg=10±1 pS. The excess current noise of the low amplitude states over $H_7$ single channel noise was modest, <5% broadening at half-width of the individual peaks in current histograms (filtered at 5 kHz), denoting an absence of unusual higher frequency events within these states. In two cases (out of seven that were analyzed), the typical low amplitude behavior (FIG. 2A and FIG. 2B) was preceded by two-state behavior with faster kinetics (Δg=7±1 pS; mean life-time of lower conductance state 709±81 ms, n=19 events; frequency of occurrence 0.32 s$^{-1}$). The faster transitions lasted for five and eight minutes before irreversible (>15 min) conversion to the typical behavior.

When the PEG was cleaved from the pore, by reduction of the disulfide bond with DTT, the current increased to a value similar to that observed with $H_7$ (FIG. 2C and FIG. 2D), after a lag period of 18–25 minutes (n=4). Long-lived low amplitude fluctuations were also observed with $H_6$K8C-PEG5$K_1$,, centered around a mean conductance of 244±19 pS (n=8) (Table 1), which is higher than the value for $H_6$S106C-PEG5$K_1$. There were typically three to five substates with life-times ranging from a few tens of milliseconds to hundreds of milliseconds. Δg values (8 pS to 50 pS) were often larger than those of the substates of $H_6$S106C-PEG5$K_1$. Strikingly, the short-lived high amplitude spikes were completely absent.

TABLE 1

Conduction properties of unaltered ($H_7$) and PEG-modified αHL pores[a]

| Channel | Mean Conductance Substates (pS)[b] | (pS)[c] | After PEG Cleavage (pS)[d] |
|---|---|---|---|
| $H_7$ | 268 ± 5 (11) | none | n.a. |
| $H_6$K8C-PEG5$K_1$ | 244 ± 19 (8) | 17 ± 4, d (8) | 270 ± 5 (8) |
| $H_6$S106C-PEG5$K_1$ | 221 ± 9 (7) | 10 ± 1, d; 120 ± 7, s (7) | 267 ± 7 (4) |
| $H_6$S106C-PEG3$K_1$ | 237 ± 4 (5) | 128 ± 3, s (5)[e] | 272 ± 3 (5) |

[a]Studies were performed at a transmembrane potential of +100 mV with 300 mM KCl, 5 mM Tris-HCl (pH = 7.00), 100 μM EDTA in both chambers. The number of studies analyzed is shown in parentheses.
[b]The mean (± s.d.) of the mean conductance values from the major peaks of all-points histograms (e.g., FIG. 2A and FIG. 2B) was calculated.
[c]The mean change in conductance (Δg ± s.d.) between the most common substates. d, discrete low amplitude events; s, negative current spikes.
[d]The conductance was determined after treatment with DTT as described in the text. When a step to an increased steady current was observed, the PEG was assumed to have left the cavity. In the case of $H_6$S106C-PEG5$K_1$, this took 18–25 min with 10–15 mM DTT.
[e]In the case of $H_6$S106C-PEG3$K_1$ low amplitude events were seen on one occasion in six studies and are not recorded in Table 1.

Single channel current measurements were also performed on $H_6$S106C-PEG3$K_1$. The preparation was contaminated with $H_7$ channels and bilayers containing them were disregarded. The mean unitary conductance of $H_6$S106C-PEG3K, was 237±4 pS (n=5), somewhat higher than that of $H_6$S106C-PEG5$K_1$. Low amplitude events were seen in only one of the six single channels that were observed. The short-lived higher amplitude negative spikes (mean life-time, 132±10 μs, n=5) were shorter than those seen with $H_6$S106C-PEG5$K_1$, were of a similar amplitude (128±3 pS, n=5) and occurred more often (26±10 s$^{-1}$,n=5). After treatment with 10 mM DTT, the PEG3000 molecule exited the cavity after 15 sec to 4 min (n=5), far more rapidly than PEG5000.

5. Interpretation of Current Fluctuations in PEG-Modified αHL Pores

The current fluctuations observed when a PEG molecule of 5000 Da is anchored within the central cavity of αHL are remarkable, compared for example with the single invariant conductance state observed when a more rigid cyclodextrin is bound non-covalently within the channel lumen (Gu et al, 1999). While switching between defined conductance states, rather than a continuum of states, was surprising, the following explanations account for the four main behaviors observed with $H_6$S 106C-PEG5$K_1$,.

First, the reduction in current carried by the main conductance states (FIG. 2A and FIG. 2B) most likely arises from changes in the properties of the electrolyte in the cavity caused by the presence of the PEG molecule. The unaltered $H_7$ pore is ohmic and only weakly ion selective, suggesting that ion transport is through a channel filled with electrolyte with properties close to that of bulk solution. The volume of the cavity is ~36,000 Å$^3$. Were the entire PEG5000 molecule within the cavity, its "concentration" would be ~23%. At this concentration, the conductivity of a solution of 100 mM KCl would be reduced by 48% (Krasilnikov et al., 1992; Bezrukov and Vodyanoy, 1993), far greater than the 18% decrease in single channel conductance observed. Nevertheless, the result is reasonable given that a hydrated PEG molecule cannot occlude the entire conductive pathway, from one entrance to another, and that the PEG chain may lie partly outside the lumen.

Second, the slow low-amplitude fluctuations in current can be ascribed to rearrangements of the PEG5000 molecule within the cavity correlated with associated movements of the protein (the fluctuations do not occur with unmodified $H_7$). Protein motions can occur over a wide range of time scales (Kay, 1998) and recently they have been observed at the single molecule level. For example, substrate fluorescence revealed fluctuations in a rate constant of cholesterol oxidase with a correlation time of about one second (Xie and Lu, 1999; Lu et al., 1998) and FRET measurements revealed fluctuations in the conformation of staphylococcal nuclease with an average time constant of 41 ms, which was increased to 133 ms with substrate bound (Ha et al., 1999).

The third phenomenon, the very slow (minutes) interconversion between related states, is also likely to be related to rearrangement of the PEG and an associated adjustment of the protein. Long-lived conformational states in proteins have been encountered previously (Xie and Lu, 1999; Xue and Yeung, 1995; Tan and Yeung, 1997). Alternative explanations are that the current fluctuations arise entirely from movements of the PEG chain or, at the other extreme, that the fluctuations can be ascribed solely to movements of the protein destabilized by the presence of the PEG. It may be possible to distinguish these possibilities experimentally. For example, if the motion of the PEG were uncoupled from the motion of the protein, the frequency and duration of the fluctuations would be independent of the point of attachment of the PEG within the central cavity.

The fourth phenomenon, the short-lived, high amplitude, negative current spikes, may represent the partial looping of the PEG5000 chain into the transmembrane barrel or into the cis opening. The millisecond duration of the states is far longer than the dwell time of free PEG molecules within the αHL pore (Bezrukov et al., 1996; Bezrukov and Kasianowicz, 1997; Bezrukov et al., 1994), but of the same magnitude as relaxation times of PEGs tethered to supported bilayers (Wong et al., 1997; Sheth and Leckband, 1997). The uniform amplitude of these events (FIG. 2A and FIG. 2B, histogram peak "s") suggests that one or the other of the two possible looping events predominates. The pore always returns to the conductance state from which it undergoes a high amplitude excursion (n=55 events), further suggesting that the low amplitude events involve protein conformational changes as well as PEG reorganization. If instead the low amplitude events purely represented states of the PEG molecule, the PEG would have to retain "memory" of them during the larger excursions.

The results obtained with PEG3000 are consistent with the interpretation of the behavior of $H_6S106C-PEG5K_1$ as outlined above. The mean conductance of $H_6S106C-PEG3K_1$ is only 12% lower than the unmodified pore (Table 1), in keeping with the lower mass of PEG3000 compared with PEG5000. The lower "concentration" of PEG within the $H_6S106C-PEG3K_1$ pore might also explain the faster release of the PEG chain by DTT. The high amplitude spikes occur about 100 times more often with $H_6S106C-PEG3K_1$, compared to $H_6S106C-PEG5K$, and are about 100 times shorter in duration, suggesting that PEG3000 is more mobile than PEG5000 within the cavity. Finally, although the interpretation of the low amplitude events is tentative, their rarity in the case of $H_6S106C-PEG3K_1$ suggests that polymer motion is less readily coupled to protein movement than it is in $H_6S$ $106C-PEG5K_1$.

In summary, this Example shows that a multisubunit protein, a heptameric transmembrane pore, can be constructed with a synthetic polymer tethered within an internal cavity. It is not currently known whether the entire polymer chain is encapsulated. Certainly, the fluctuations of current passing through a single pore in a transmembrane potential suggest that the PEG chain is flexible and may therefore sample the external solvent. This suggests that current recording is a useful tool for monitoring the dynamic properties of PEG and other polymers, including oligopeptides and oligonucleotides, at the single molecule level. Further, by using polymers that respond to analytes, it is possible to make biosensors (Braha et al., 1997; Gu et al, 1999) based on this new class of engineered pores. This does not depend on a detailed interpretation of the current fluctuations, only that they are modulated by analytes in a concentration dependent manner and at the same time provide analyte-specific signatures (Braha et al., 1997; Gu et al., 1999).

EXAMPLE 2

Transmembrane Movement of a Single Polymer Chain Tethered Within a Protein Pore

In this Example, a protein-based structure is described in which a single functionalized polymer chain is attached at a defined site within the central cavity of a transmembrane pore built by the self-assembly of staphylococcal α-hemolysin subunits. The untethered end of the chain is capable of translocation across the membrane, from one entrance of the pore to the other, a distance of at least 10 nm. Hence, the engineered pore comprises an unusual nanostructure with a moveable part. In addition, the pore can be used to examine polymer motions on the microsecond timescale. Furthermore, it is demonstrated that the pore acts as a new type of biosensor element in which polymer-ligand conjugates are covalently attached to protein pores. A change in the ionic current carried by the pore occurs when a protein analyte binds to the functionalized polymer.

A. Materials and Methods

1. Formation of Heteromeric αHL Pores Containing Covalently-Attached PEG-Biotin

The mutant αHL genes, S106C, K8C and K8A, have been described previously (Walker and Bayley, 1994; Walker and Bayler, 1995a; Cheley et al., 1999). $^{35}$S-labeled S106C, K8C and K8A polypeptides were obtained by in vitro transcription and translation (Walker et al., 1992). To obtain a higher yield of protein, unlabeled methionine was included in the expression mix (Cheley et al., 1999; Walker et al., 1992). αHL monomers S106C and K8C were covalently modified by five-fold dilution of the translation mix into 10 mM MOPS, pH 7.0 (NaOH), containing 150 mM NaCl, 0.5 mM EDTA, reduction with 0.5 mM DTT for 5 min and reaction with 10 mM with biotin-PEG3400-maleimide (Shearwater Polymers, Huntsville, Ala., USA) for 10 min and room temperature. Modified subunits were mixed in various ratios with unmodified K8A αHL monomers (H) and allowed to assemble into heteroheptamers on rabbit erythrocyte membranes (Cheley et al., 1999; Walker et al., 1992). αHL heptamers are stable in SDS unless heated (Walker and Bayley, 1995b) and were analyzed by SDS-PAGE and autoradiography. Where indicated a large excess (8.5 mg/ml) of streptavidin (S-4762, Sigma) was added prior to analysis. Heptameric pores for electrical recording were obtained from preparative gels (Braha, 1997). The ratios of unmodified to modified subunits in these purified proteins were determined by heating the proteins to 95° C. and separating the dissociated subunits in a second, analytical gel (Example 1).

2. Bilayer Recording

The formation of bilayers of 1,2-diphytanoyl-sn-glycerophosphocholine (Avanti Polar Lipids), the insertion of heptameric αHL pores into them, and single-channel recording have been described (Braha, 1997; Montal and Mueller, 1972). Both the cis and trans chambers of the apparatus contained 300 mM KCl, 5 mM Tris-HCl, pH 7.00, with 100 µM EDTA. αHL pores were added to the cis chamber, at a concentration of 0.05–0.3 ng/ml. The solution was stirred for ~15 minutes until a single channel inserted into the bilayer. Currents were recorded by using a patch clamp amplifier (Axopatch 200B, Axon Instruments) at a holding potential of +100 mV (with the cis side grounded). The signals were low-passed filtered with a built-in 4-pole Bessel filter at a frequency of 10 kHz and recorded on digital audio tape recorder. For computer analysis, the signals were further filtered with an 8-pole Bessel filter at frequencies in the range 1–4 kHz and sampled at 20 kHz, unless otherwise specified.

Statistical analysis was carried out by using the FETCHAN and pSTAT programs, both from the software package pCLAMP7 (Axon Instruments), and Origin (Microcal Software). Measurements are given as mean ±s.d. $k_{off}^{cis}$ values were obtained from $1/\tau_{off}$, determined from dwell-time histograms. $k'_{on}{}^{cis}$ values were determined from the concentration dependence of $1/\tau_{on}$. Because relatively few events were recorded, $k_{off}^{trans}$ and $k'_{on}{}^{trans}$ values were determined from mean dwell times and mean inter-event intervals. For cis events, 'n' refers to the number of studies. For trans events, 'n' refers to the number of events.

3. Molecular Graphics

The molecular models of streptavidin (lswd.pdb) and α-hemolysin (7ahl.pdb) were generated with SPOCK 6.3 software (Christopher, 1998).

B. Results

For applications in biotechnology, engineered versions of αHL have been prepared that contain built-in triggers and switches actuated by physical, chemical and biochemical stimuli (Chang et al., 1995; Panchal et al., 1996; Russo et al., 1977). In addition, genetically engineered αHL and αHL in combination with non-covalent molecular adapters have been used as stochastic sensor elements to monitor individual metal ions (Braha et al., 1997) and small organic molecules (Gu et al., 1999).

The interactions of polymers with various pores including αHL have been studied extensively (Bezrukov et al., 1994; Bezrukov et al., 1996; Merzlyak et al., 1999). Especially appealing is the use of electrical recording to count polyanionic DNA and RNA strands as they move through the αHL pore in a transmembrane potential (Kasianowicz et al., 1996; Akeson et al., 1999). Information about the length and base composition of the polynucleotides is obtained by monitoring the electrical current while the polymers are in the channel. Single neutral polyethylene glycol molecules of 3400 Da have now been observed, by tethering them within the lumen of the αHL pore. By measuring the current passing through the pore, the structural dynamics of the polymer chain can be monitored. The polymer contains a biotinyl group at the untethered end and by using genetically engineered streptavidin mutants with a weakened binding affinity (Sano and Cantor, 1995; Chilkoti et al., 1995a), the appearance of the biotin on both the cis and trans side of the membrane can be monitored during a single study.

A preparation of heptameric αHL pores was made, which was enriched in molecules containing six unmodified subunits and one subunit covalently modified within the central cavity with PEG-biotin. $^{35}$S-labeled PEG-biotin-modified heteroheptameric αHL pores were analyzed by SDS-PAGE and autoradiography. Where required, the samples were treated with excess WT-streptavidin before electrophoresis. Ratios of unmodified and modified subunits in the initial assembly mix included 6:1, 1:6 and 4:3. The components of each band could be inferred from band shifts after streptavidin treatments and dissociation of the subunits by heating followed by additional electrophoresis.

Heptamers obtained by co-assembly (Braha et a/, 1997; Example 1) of unmodified αHL and the mutant SI 06C, which had been reacted with biotin-PEG3400-maleimide, co-migrated with unmodified heptamers upon SDS-polyacrylamide gel electrophoresis. The addition of streptavidin (60 kDa) before electrophoresis caused ~75% of the material to migrate more slowly. This more slowly migrating material contained heteroheptamers with six unmodified and one modified subunit ($H_6$106C-PEG-biotin,), according to a second analysis by SDS-PAGE performed after heating the sample to dissociate the subunits. No band corresponding to heteroheptamers with two modified subunits was detected in the streptavidin-treated assembly products, but such a band was present in a preparation of heteroheptamers derived from the mutant K8C modified with PEG-biotin.

Position 8 is near the cis entrance to the channel lumen and PEG molecules on all seven subunits can be tolerated at this position (Example 1). Because $H_6$106C-PEG-biotin, co-migrates with unmodified heptamers ($H_7$), it is inferred that the bulk of the PEG chain remains within the central cavity of the pore where it has no appreciable effect on electrophoretic mobility. By contrast, a single PEG5000 chain attached at position 106 increases the electrophoretic mobility of the heptamer and must protrude into the extralumenal solvent (Example 1).

The single channel properties of $H_6$ 106C-PEG-biotin, were examined by planar bilayer recording. Currents arising from the contaminating $H_7$ pores, which had the same conductance as control $H_7$ pores (271±3 pS, n=14), were disregarded. The results of the bilayer studies are shown in Table 2, Table 3, Table 4 and Table 5 below.

TABLE 2

Conduction Properties of Unaltered ($H_7$) and PEG-modified αHL Pores[a]

| Channel | Mean Conductance (pS)[b] | Short-Lived and High-Amplitude Closures | | |
|---|---|---|---|---|
| | | Life Time (µs) | Amplitude (pS) | Frequency of Occurrence (s$^{-1}$) |
| $H_7$ | 271 ± 3 (14) | NA | NA | NA |
| $H_6$S106C-PEG-biotin$_1$ | 229 ± 4 (17) | 130 ± 7 (17) | 121 ± 4 (17) | 37 ± 6 (17) |
| $H_6$S106C-PEG3K$_1$ | 237 ± 4 (5) | 132 ± 10 (5) | 128 ± 3 (5) | 26 ± 10 (5) |

[a]Studies were carried out with symmetrical electrolyte solutions (300 mM KCl, 5 mM Tris-HCl, 100 µM EDTA, pH = 7.00 ± 0.01) at an applied transmembrane potential of +100 mV. The number of studies analyzed is indicated in parentheses.
[b]The mean (± s.d.) of the mean conductance values were derived from the major peaks of all-point single-channel current histograms of individual studies.

TABLE 3

Conduction Properties of $H_6S106C$-PEG-biotin$_1$
Upon Addition of Wild-Type Streptavidin to the cis or trans Chamber[a]

| Chamber Added[b] | Mean Conductance | | Relative Channel Block[c] |
|---|---|---|---|
| | Before Addition of Streptavidin (pS) | After Addition of Streptavidin (pS) | |
| cis | 221 ± 12 (4) | 224 ± 12 (4) | 0% |
| trans | 230 ± 4 (5) | 110 ± 9 (5) | 51.3 ± 3.3% |

[a]Studies were carried out with symmetrical electrolyte solutions (300 mM KCl, 5 mM Tris-HCl, 100 μM EDTA, pH = 7.00 ± 0.01) at an applied transmembrane potential of +100 mV. All numbers from the table represent ± s.d. For cis events, the number in parentheses refers to the number of studies. For trans events, number in parentheses refers to the number of events.
[b]The final concentration of wild-type streptavidin in the cis or trans chamber covered the range of 12–72 nM.
[c]Relative channel block is the channel block accompanied by the binding of streptavidin relative to the mean conductance before addition of streptavidin.

TABLE 4

Conduction Properties of $H_6S106C$-PEG-biotin$_1$
Upon Addition of Streptavidin Mutant W120A
to the cis or trans Chamber[a]

| Chamber Added[b] | $t_{on}$ (ms) | $t_{off}$ (ms) | Relative Channel Block[c] |
|---|---|---|---|
| cis | 4750 ± 230 (6) | 3180 ± 140 (6) | 0% |
| trans | 318800 ± 54000 (5) | 677 ± 476 (5) | 52.4 ± 4.1% |

[a]Studies were carried out with symmetrical electrolyte solutions (300 mM KCl, 5 mM Tris-HCl, 100 μM EDTA, pH = 7.00 ± 0.01) at an applied transmembrane potential of +100 mV. All numbers from the table represent ± s.d. For cis events, the number in parentheses refers to the number of studies. For trans events, number in parentheses refers to the number of events.
[b]The protein concentration of W120A streptavidin in the cis or trans chamber was 7.25 nM.
[c]Relative channel block is the channel block accompanied by the binding of streptavidin relative to the mean conductance before addition of streptavidin.

TABLE 5

Conduction Properties of $H_6S106C$-PEG-biotin$_1$
Upon Addition of Anti-Biotin mAb to the cis or trans Chamber[a]

| Chamber Added[b] | $t_{on}$ (ms) | $t_{off}$ (ms) | Relative Channel Block[c] |
|---|---|---|---|
| cis | 4750 ± 230 (6) | 3180 ± 140 (6) | 0% |
| trans | 318800 ± 54000 (5) | 677 ± 476 (5) | 52.4 ± 4.1% |

[a]Studies were carried out with symmetrical electrolyte solutions (300 mM KCl, 5 mM Tris-HCl, 100 μM EDTA, pH = 7.00 ± 0.01) at an applied transmembrane potential of +100 mV. All numbers from the table represent ± s.d. For cis events, the number in parentheses refers to the number of studies. For trans events, number in parentheses refers to the number of events.
[b]The protein concentration of anti-biotin mAb in the cis chamber was 1.8 nM, the concentration in the trans chamber was 5.8 nM.
[c]Relative channel block is the channel block accompanied by the binding of streptavidin relative to the mean conductance before addition of streptavidin.

Figure 3A:
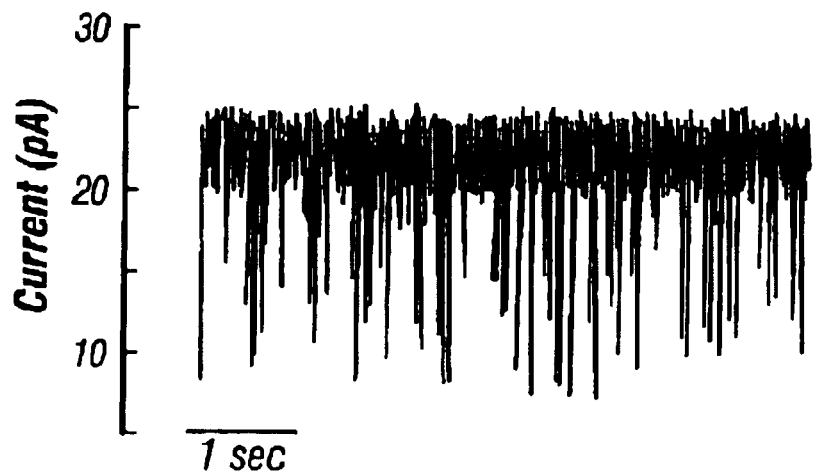
FIG. 3A and FIG. 3B. Single channel properties of the heteromeric pore $H_6106C$-PEG-biotin$_1$.
Figure 3B:
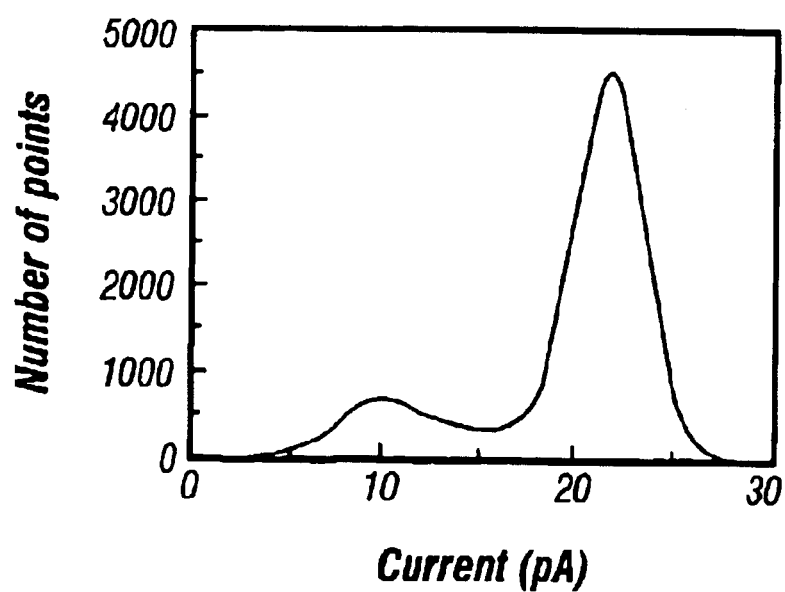
Figure 4A:
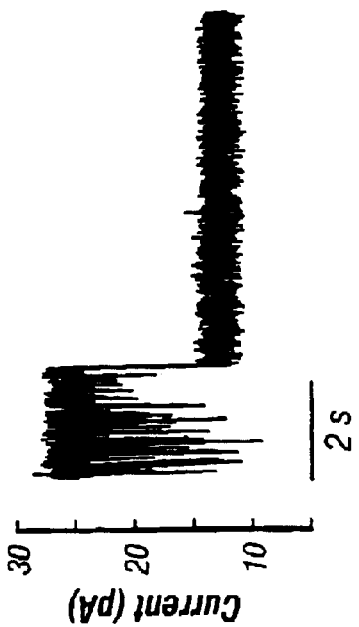
Figure 4C:
Figure 4B:
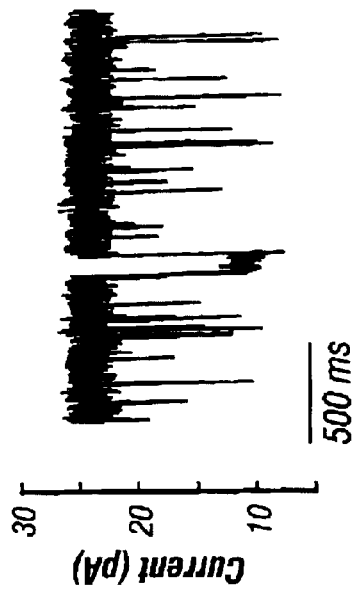

The $H_6$106C-PEG-biotin, channels exhibited a reduced unitary conductance state (229±4 pS, n=17) decorated with short-lived high-amplitude negative spikes (mean life time, 130±7 μs, amplitude, 121±4 pS, n=17), which occurred at a high frequency (37±6 s$^{-1}$, n=17) (FIG. 3A and FIG. 3B). Both the reduced conductance and the spikes were associated with the PEG chain (rather than the biotin), as $H_6$106C-PEG3K$_1$ channels, which contain a PEG of 3000 Da without the biotinyl group, showed very similar characteristics (unitary conductance 237±4 pS; spike life time, 132±10 μs; amplitude, 128±3 pS; frequency, 26±10 s$^{-1}$, n=5). When 12 nM wild-type (WT) streptavidin was added to the cis side of a bilayer containing a $H_6$106C-PEG-biotin, pore, the spikes disappeared completely after a short lag period (117±11 s, n=4), leaving the mean conductance unchanged (FIG. 4A). By contrast, the addition of 12 nM WT streptavidin to the trans side of the bilayer caused a permanent partial channel block of 120±9 pS (n=5) (FIG. 4B). The extent of the block (51±3%, n=5) was closely similar to the average amplitude of the short-lived spikes (121±4 pS, 53±2%, n=17) and occurred after a lag period of 158±29 s (n=5). The above results are interpreted as the essentially permanent capture of the PEG-biotin chain by WT streptavidin ($K_d$=4×10$^{-14}$ M in solution (Chilkoti et al., 1995a)) at the trans or cis side of the bilayer.

Figure 4D:
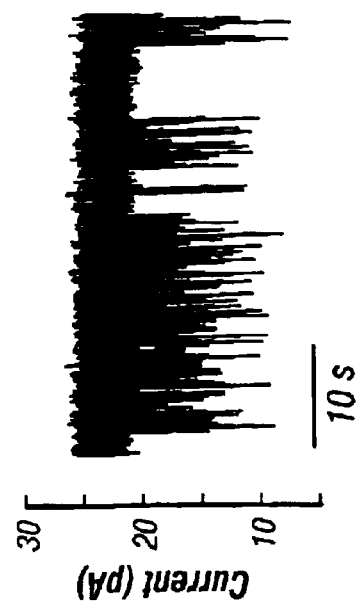
Figure 4F:
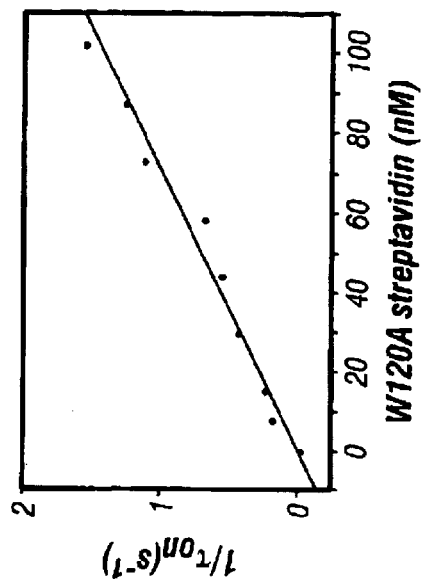
Figures 1, 4E:
Figures 2, 4E:
Figures 3, 4E:
Figure 4H:
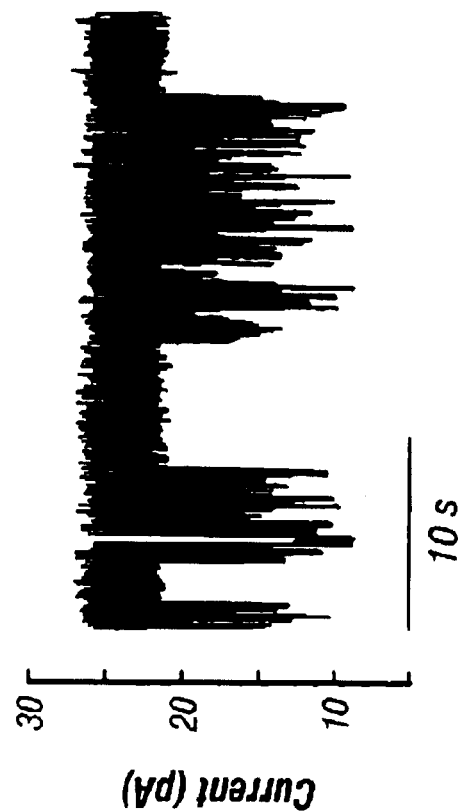
Figure 4G:
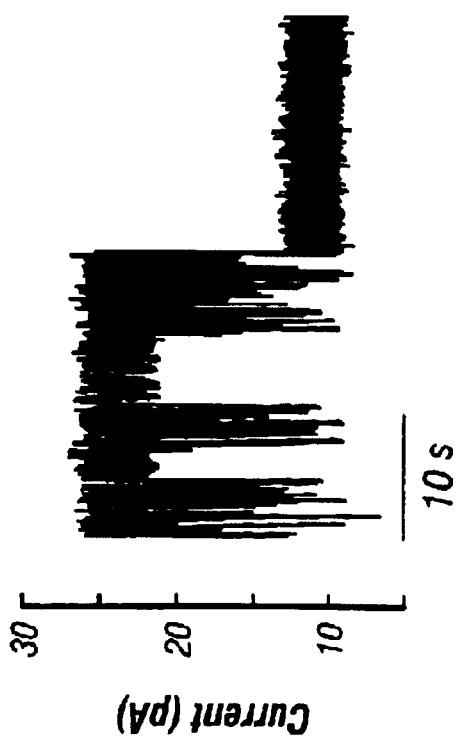

When W120A streptavidin, a mutant with considerably lower affinity for biotin ($K_d$=1.1×10$^{-7}$ M (Chilkoti et al., 1995a; Chilkoti et al., 1995b; Perez-Luna et al., 1999)) was added to the trans or cis side of the $H_6$106C-PEG-biotin, pore, transient instead of permanent disappearances of the spikes were observed (FIG. 4C and FIG. 4D). However, in terms of the extent of channel block, the transient binding events brought about by W120A were closely similar to those seen with WT streptavidin (FIG. 3A and FIG. 3B): no measurable block on the cis side, and a 52±4% block on the trans side. As expected for a bimolecular interaction, the frequency of occurrence of blocking events ($1/\tau_{on}$=$k_{on}$[W120A]) was proportional to the concentration of W120A (FIG. 4E-1, FIG. 4E-2, FIG. 4E-3 and FIG. 4F). Remarkably, sequential binding events of W120A streptavidin from both sides of the bilayer were able to be monitored in a single study, due to the different signatures of the trans and cis events (FIG. 4G and FIG. 4H).

At identical protein concentrations, the reversible binding events of W120A streptavidin occurred more than 50 times less frequently at the trans side than at the cis side. In addition, the trans events exhibited a shorter dwell time. Through the analysis of inter-event intervals ($\tau_{on}$) and event lifetimes ($\tau_{off}$), apparent kinetic constants (k') for the association and true kinetic constants (k) for the dissociation of the W120A streptavidin.biotin complex were obtained for each side of the lipid bilayer in 300 mM KCl, 5 mM Tris-HCl, pH 7.00, containing 100 μM EDTA at +100 mV: $k'_{on}{}^{cis}$=0.38±0.03×10$^7$ M$^{-1}$ s$^{-1}$ (all $k'_{on}$ values for streptavidin are corrected for the presence of four biotin binding sites on each protein); $k_{off}{}^{cis}$=0.31±0.01 s$^{-1}$; $K'_d{}^{cis}$=0.82±0.02×10$^{-7}$ M; $k'_{on}{}^{trans}$=1.08±0.15×10$^5$ M$^{-1}$ s$^{-1}$; $k_{off}{}^{trans}$=1.48±0.61 s$^{-1}$; $K'_d{}^{trans}$=1.37±0.56×10$^{-5}$ M. The value of $K'_d{}^{cis}$ is closely similar to the reported $K_d$ value (1.1×10$^{-7}$ M) (Chilkoti et al., 1995a).

Figure 5A:
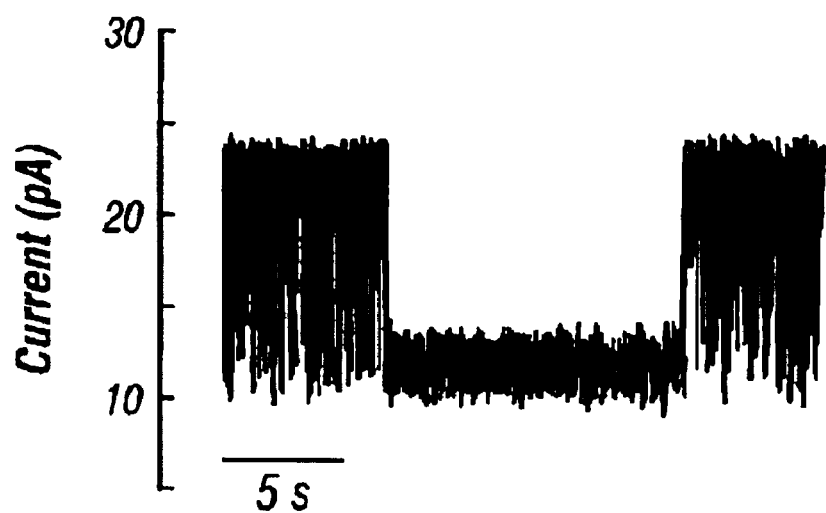
FIG. 5A and FIG. 5B. Response of $H_6106C$-PEG-biotin, to a mouse anti-biotin monoclonal IgG$_1$ (mAb). Single-channel current recordings. Thick bars show trans biotin capture events and the thin bars cis events. The biotin-binding proteins were added before the start of each trace.

Similar findings were obtained with a mouse anti-biotin monoclonal IgG$_1$ (mAb). For example, application of the mAb to the cis side of a bilayer containing $H_6$106C-PEG-biotin, was accompanied by the transient disappearance of the spikes but did not alter the amplitude of the main conductance state. Because all three biotin-binding proteins fail to alter the unitary conductance when they bind on the cis side of the bilayer, it is likely that a major fraction of the PEG chain remains within the αHL cavity during cis captures. By contrast, biotin capture by the mAb at the trans side of the bilayer led to a drop in the mean conductance of 55±2% (FIG. 5A), close to the value for W120A the streptavidins (W120A, 52±4%. WT, 51±3%). Because both the streptavidins and the mAb produce a similar block, it is likely that the physical origin of the block derives from the PEG chain passing through the inner restriction, rather than from the binding protein itself.

Figure 5B:
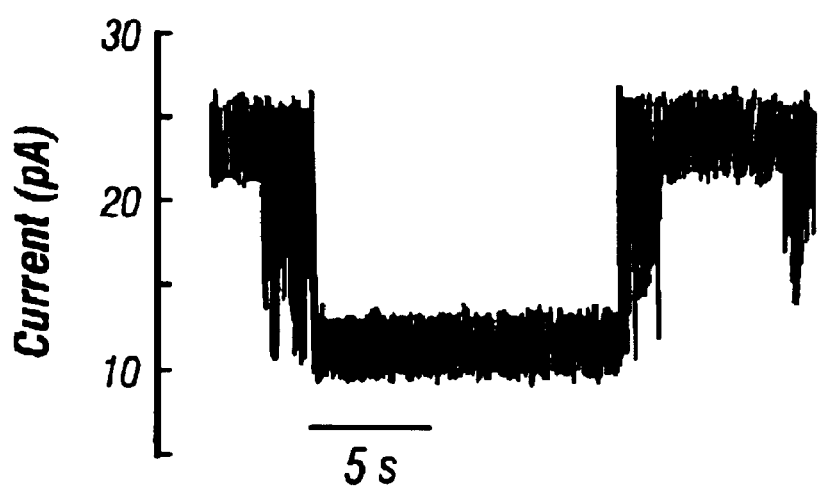

Kinetic constants for the association and dissociation of the mAb were obtained for both sides of the lipid bilayer in 300 mM KCl, 5 mM Tris-HCl, pH 7.00, containing 100 μM EDTA at +100 mV: $k'_{on}{}^{cis}$=4.86±1.02×10$^7$ M$^{-1}$ s$^{-1}$ (all $k'_{on}$ values for the mAb are corrected for the presence of two biotin binding sites on each protein); $k_{off}{}^{cis}$=0.019±0.003 s$^{-1}$; $K'_d{}^{cis}$=0.39±0.06×10$^{-9}$ M; $k'_{on}{}^{trans}$=4.32±1.01×10$^5$ M$^{-1}$ s$^{-1}$; $k_{off}{}^{trans}$ 2.88±0.74×10$^{-2}$ s$^{-1}$; $K'_d{}^{trans}$=0.66±0.16×10$^{-7}$ M. Again, biotin-binding events could be observed on both sides of the bilayer in a single study. Indeed, captures by two different biotin-binding proteins were recorded, e.g., cis: W120A streptavidin, trans: mAb (FIG. 5B).

The results with both W120A streptavidin and the monoclonal antibody are consistent with a simple kinetic model. In such a kinetic model of the interactions between the αHL pore H$_6$106C-PEG-biotin, and streptavidin at the cis and trans sides of the bilayer, let $p_{cis}$ and $P_{trans}$ be the probabilities that the biotinyl group is on the cis and trans sides of the bilayer. $P_{inside}$ is the probability that it is in the lumen of the αHL pore. Assuming that the equilibria are not disturbed by biotin capture, $P_{cis}/P_{inside}=k_+{}^{cis}$, $P_{trans}/P_{inside}=k_+{}^{trans}/k_-{}^{trans}$, and $P_{cis}+P_{trans}+P_{inside}=1$. Therefore, $P_{inside}(1+k_+{}^{cis}/k_-{}^{cis}+k_+{}^{trans}/k_-{}^{trans})=1$, $P_{cis}=k_+{}^{cis}/k_-{}^{cis}(1+k_+{}^{cis}/k_-{}^{cis}+k_{trans}/k_{trans})$, and $p_{trans}=k_+{}^{trans}/k_-{}^{trans}(1+k_+{}^{cis}/k_-{}^{cis}+k_+{}^{trans}/k_-{}^{trans})$. Let $k_+{}^{trans}/k_-{}^{trans}$ be small based on the finding that appearances on the trans side of the bilayer are infrequent. Then $P_{cis}=k_+{}^{cis}/(k_-{}^{cis}+k_+{}^{cis})$, $P_{trans}=(k_+{}^{trans}/k_-{}^{trans})(k_-{}^{cis}/(k_-{}^{cis}+k_+{}^{cis}))$, and $P_{cis}/P_{trans}=(k_+{}^{cis}/k_-{}^{cis})(k_+{}^{trans}/k_-{}^{trans})$. For capture, $k_{off}/k'_{on}=K'_d$, kinetic constants as measured herein, $k_{off}/k_{on}=K_d$, actual kinetic constants, $k'_{on}{}^{cis}=p_{cis}k_{on}{}^{cis}$, $k'_{on}{}^{trans}=p_{trans}k_{on}{}^{trans}$, $K_d{}^{cis}=p_{cis}K'_d{}^{cis}$, $K_d{}^{trans}$, $p_{trans}=K'_d{}^{trans}$, and $P_{cis}/P_{trans}=(K_d{}^{cis}/K_d{}^{trans})(K'_d{}^{trans}/K'_d{}^{cis})$. In the cases examined, $K'_d{}^{cis} \neq K_d{}^{cis}$, $P_{cis}\sim1$, $K_d{}^{trans}>>1$, and $p_{cis}/p_{trans}\sim150$.

As the biotinyl group is rarely captured on the trans side of the bilayer, $k_+{}^{trans}$ is likely relatively small. Therefore, the fraction of time spent by the biotinyl group on the cis side is given by $P_{cis}=k_+{}^{cis}/(k_-{}^{cis}+k_+{}^{cis})$ and the fraction of time spent on the trans side by $P_{trans}=(k_+{}^{trans}k_-{}^{trans})\times(k_-{}^{cis}+k_-{}^{cis}+k_+{}^{cis}))$. In terms of measurable dissociation constants $K_d{}^{cis}=p_{cis}K'_d{}^{cis}$ and $K_d{}^{trans}=p_{trans}K'_d{}^{trans}$. Therefore:

$$p_{cis}/p_{trans}=(K_d{}^{cis}/K_d{}^{trans})\times(K'_d{}^{trans}/K'_d{}^{cis}) \quad (1)$$

Assuming that the dissociation constants for the biotin-streptavidin interaction are the same as those determined under other circumstances (Chilkoti et al., 1995a) and the same on both sides of the bilayer ($K_d{}^{cis}=K_d{}^{trans}$), then $P_{cis}/P_{trans}$=167±68. The latter assumption is not strictly true; for example, for streptavidin W120A, $k_{off}{}^{trans}$ is about five times larger than $k_{off}{}^{cis}$; perhaps elongation of the PEG chain lowers the activation barrier for dissociation. While the value of $p_{cis}/p_{trans}$ is approximate, it does provide a qualitative picture of biotin localization with respect to the bilayer. Gratifyingly, equation 1 yields a similar value of $P_{cis}/P_{trans}$=169±41 for studies with the mAb.

When the biotinyl group is captured on the cis side of the bilayer by the streptavidins or the mAb, there is no detectable change in channel conductance suggesting that the PEG chain is still largely contained within the central cavity, where it reduces the flow of ions by about 15.5% (Example 1), and that the streptavidin molecule does not itself perturb current flow. By contrast, capture on the trans side is accompanied by a dramatic reduction in single channel conductance that is strikingly similar in amplitude to the current reduction seen during the transient current spikes that occur in the absence of the biotin-binding proteins or between captures in their presence. This similarity indicates that the spikes represent excursions of the biotinyl group towards the trans entrance into the transmembrane β-barrel. In accordance with this interpretation, there is a complete absence of spikes during the cis capture events when the end of the polymer is unavailable for threading into the barrel. The spikes occupy about 0.48% of the current trace in the absence of streptavidin, which is roughly in accord with the value of $P_{cis}/P_{trans}$, therefore, the frequency of occurrence of the spikes of 37±6 s$^{-1}$ is likely to be the upper limit for the rate of appearance at the trans entrance and for transmembrane movement (appearances at the cis entrance being yet more frequent but electrically silent).

In summary, a nanoscale protein pore was assembled with a covalently-attached and functionalized moving arm. The untethered end of the arm is free to move across the bilayer from one mouth of the pore to the other, a distance of more than 10 nm. Despite the great interest in nanostructures, few assemblies with moving parts have been made; one recent achievement is a nanomechanical device based on the B-Z transition of DNA (Mao et al, 1999). The functionalized pore of the present invention can also include the ability to control the position of the arm, for example with the transmembrane potential, which can be used to drive transmembrane transport. This system is also applicable to examining the dynamics of polymers other than PEG at the single molecule level, including biological molecules such as polynucleotides, oligosaccharides and peptides.

The characterization of single polymer molecules is active area of research, which is usually limited to optical microscopy or force measurements (Weiss, 1999; Mehta et al., 1999; Xie and Lu, 1999; Marszalek et al., 1999). Finkestein and colleagues have examined the transmembrane movement of biotinylated toxins by capture with streptavidin (Slatin et al., 1994), and the inventors contemplate that biotin-binding proteins with reduced affinity, might have advantages in such studies, as demonstrated herein. Finally, these results show how engineered protein pores can be used, at the single-molecule level, as stochastic sensor elements for protein analytes. The present invention thus shows that proteins such as antibodies can be detected at low nanomolar concentrations (e.g., FIG. 4F) by using a chemically modified pore. Stimulus-responsive polymers (Stayton et al., 1995) can also be attached in the channel lumen to yield another class of sensor elements.

EXAMPLE 3

Sequence-Specific Detection of DNA Using Engineered Protein Pores

The present example shows various means of applying the present invention to the field of DNA biochemistry. A single-stranded DNA (ssDNA) molecule was covalently attached to the (x-hemolysin pore of Staphylococcus aureus. Changes in the current flowing through an engineered pore revealed the sequence-specific binding of individual ssDNA molecules to the tethered DNA strand. The DNA-nanopore was able to discriminate, at the single molecule level, between DNA strands up to 30 nucleotides in length differing by a single base substitution. The use of the nanopore as a biosensor element was exemplified by the detection of a drug resistance-conferring mutation in the reverse transcriptase gene of HIV. In addition, the present example demonstrates the use of such DNA-nanopore compositions to sequence codons in tethered DNA-strands. This example therefore shows the application of the covalently modified nanopore technology of the invention in the generation of nanopores modified with ssDNA or RNA and the use of such oligonucleotide-nanopores to sense and sequencing DNA molecules by single molecule detection.

The examination of individual RNA or DNA molecules is a thriving area of research. Individual polynucleotide molecules can be studied by fluorescence correlation spectroscopy (Eigen and Rigler, 1994; Kinjo et al., 1998), force measurements (Strunz et al., 1999; Baumann et al., 2000; Smith et al., 1996), and electrical recordings (Andersen, 1999; Deamer and Akeson, 2000; Henrickson et al., 2000). In electrical recordings, a single strand of RNA or DNA is driven by an applied potential through a single nanopore, which leads to a detectable change in the ionic current flowing through the pore (Kasianowicz et al., 1996). This approach has been employed to discriminate between RNA and DNA homo- or block polymers with different base compositions (Akeson et al., 1999; Meller et al., 2000). However, the single base resolution required to sequence individual strands of DNA has been so far elusive. In these aspects of the invention, the sensitivity of single channel current recording is surprisingly combined with the selectivity of nucleic acid hybridization (Taton et al., 2000; Lipshutz et al., 1999) to sense the binding of individual DNA molecules to a DNA strand tethered to a nanopore.

In heptameric pores of αHL, the 293 amino acid monomeric polypeptide assembles to form a known structure (Song et al., 1996) resembling a mushroom of 10 nm in height and up to 10 nm in width. The lumen of αHL measures 3 nm at the cis entrance, widens to 4.1 nm in the internal cavity and narrows at the inner constriction to a diameter of 1.6 nm. In the transmembrane barrel, the lumen has an average diameter of 2 nm. Because of the narrow inner constriction, ssDNA but not double stranded DNA (dsDNA) can pass through the pore (Kasianowicz et al., 1996). Molecular graphics simulations reveal, however, that the internal cavity is big enough to accommodate a DNA duplex 10 base pairs (bp) in length.

A. Materials and Methods

1. Formation of Heteromeric αHL Pores Containing Covalently-Attached Oligonucleotides An αHL pore carrying a single DNA oligonucleotide attached to a site located at the cis entrance of the lumen was generated. The DNA-nanopore was composed of six unmodified subunits and one subunit covalently modified with the oligonucleotide. Heptamers with this composition were obtained by assembly of unmodified αHL (H) and the cysteine mutant 17C-D4, which had been coupled through a disulfide linkage to oligo-A (5'-CATTCACC-3'; SEQ ID NO:1), 8 nucleotides (nt) in length.

To achieve this, oligonucleotides were first activated and then reacted with the single cysteine residue of αHL-17C-D4. 5' thiol-modified DNA oligonucleotides with a hexamethylene linker were purchased from Research Genetics (Huntsville, Ala.) and activated with 2,2'-dipyridyl disulfide to yield 5'-S-thiopyridyl oligonucleotide (Corey et al., 1995) for coupling to the protein. The mutant αHL-17C-D4 was generated by site-directed mutagenesis (Howorka and Bayley, 1998) of the engineered gene αHL-WT-RL-D4, which encodes the wild-type αHL protein and a C-terminal polypeptide extension of four aspartate residues. $^{35}$S-labeled αHL polypeptides H (wild type) and 17C-D4 were generated by expression in vitro (Cheley et al., 1999).

Figure 6A:
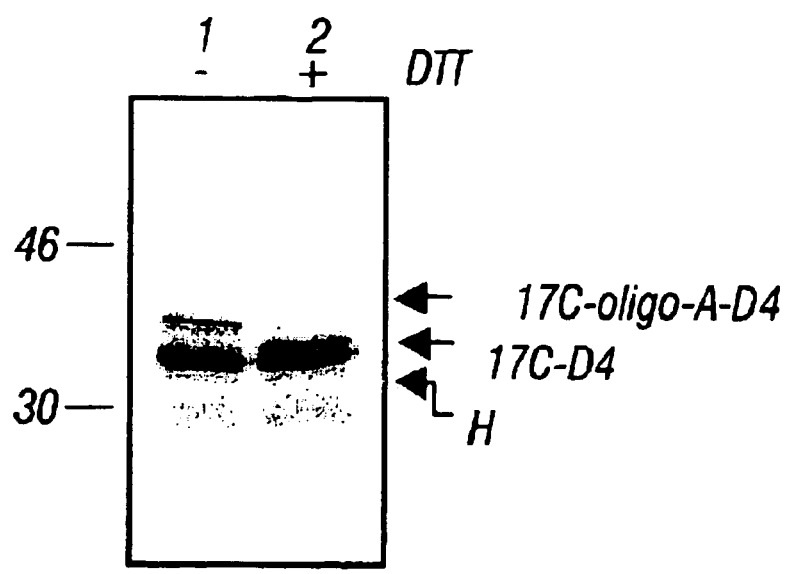
FIG. 6A and FIG. 6B. Attachment of a single DNA oligonucleotide to the αHL pore. In the heteroheptameric αHL pore, containing six unmodified and one DNA-modified subunit, the 5'-end of the oligonucleotide is tethered via a hexamethylene linker and a disulfide bond to Cys$^{17}$ introduced by mutagenesis. An applied, positive electrical potential drives negatively charged molecules from the cis to the trans side of the bilayer.

For the coupling to oligonucleotides, translation mixes of 17C-D4 (3 μl, 300 ng λHL protein) and of H (15, 1, 1.5 μg) were combined and separated from excess β-mercaptoethanol by using spin filter columns with a molecular weight cut off of 10 kDa (#42407, Millipore). For this treatment, the combined mixes were diluted into 0.1 mM DTT (0.5 ml) and concentrated by centrifugation to a volume of 30 μl. The procedure was repeated two times. The retentate (30 μl) was then diluted 2-fold into a buffer containing 10 mM MOPS-NaOH, pH 7.4, 150 mM NaCl, 0.5 mM EDTA and reacted with 50 nmol 5'-S-thiopyridyl oligonucleotide for 10 min at 25° C. The monomeric subunits were then co-assembled on rabbit erythrocyte membranes (Walker et al., 1992a) and the resultant heptamers were purified by SDS-polyacrylamide gel electrophoresis (Howorka et al., 2000; FIG. 6A).

Figure 6B:
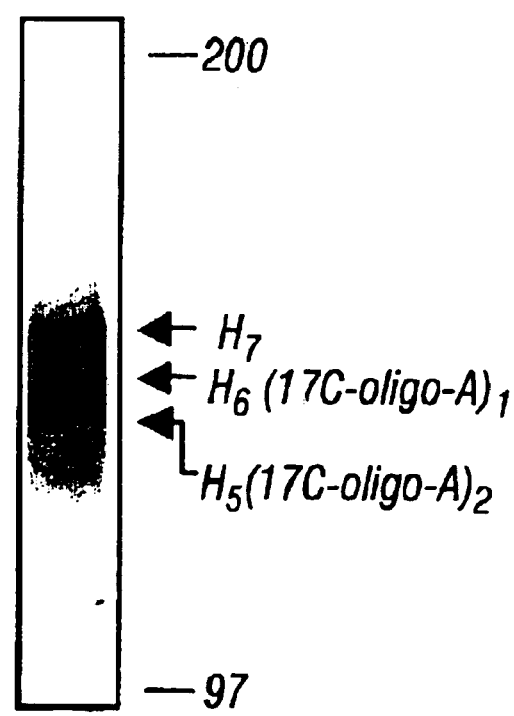

Heteroheptamer $H_6(17C\text{-oligo-A})_1$ was purified from heptamers $H_7$ and $H_5(17C\text{-oligo-A})_2$, which also formed during the assembly process, by SDS-PAGE (FIG. 6B). In this, the various heptamers migrated in separate bands by virtue of a gel shift caused by a C-terminal polypeptide extension of four aspartates (D4), present only in 17-oligo-A-D4 but not in the H subunits. Interestingly, the modification of C-D4 with DNA caused the monomer to migrate more slowly (FIG. 6A, compare lanes 1 and 2), but did not alter the electrophoretic mobility of the heptamer.). The subunit ratio in heteroheptamer $H_6(17C\text{-oligo-A})$, was confirmed by additional SDS-PAGE after the protein had been extracted from the first gel and heated to dissociate the subunits.

2. Bilayer Recordings

Planar lipid bilayer recordings were used to examine the single-channel properties of $H_6(17C\text{-oligo-A})$, and its interaction with oligonucleotides of complementary sequence added to the cis chamber. These recordings were carried out at 22±1° C. (Braha et al., 1997). Briefly, a bilayer of 1,2-diphytanoyl-sn-glycerophosphocholine (Avanti Polar Lipids, Alabaster, Ala.) was formed on an aperture (140 μm in diameter) in a Teflon septum (Goodfellow Corporation, Malvern, Pa.), which separated the cis and trans chambers (1.5 ml each) of a planar bilayer apparatus. The electrolyte in both chambers was 2 M KCl, 12 mM $MgCl_2$ and 5 mM Tris-HCl, pH 7.4. Heptameric αHL protein was added to the cis chamber, at a concentration of 0.01 to 0.1 ng/ml, and the electrolyte in the cis chamber stirred until a single channel inserted into the bilayer. Electrical recordings were performed at a holding potential of +100 mV (with the cis side grounded) by using a patch clamp amplifier (Axopatch 200B, Axon Instruments, Foster City, Calif.). Currents were low-pass filtered with a built-in 4-pole Bessel filter at 10 kHz and sampled at 50 kHz by computer with a Digidata 1200 A/D converter (Axon Instruments) and analyzed (Movileanu et al., 2000). Traces shown in the figures were filtered at 1 kHz and sampled at 5 kHz. Unless otherwise stated, DNA oligonucleotides were purchased from Integrated DNA Technologies (Coralville, Iowa) and used without further purification.

The channels were analyzed under an electric field of +100 mV, which drives negatively charged molecules such as DNA from the cis to the trans side of the bilayer. In 2 M KCl, 12 mM $MgCl_2$ and 5 mM Tris-HCl, pH 7.4, the unitary conductance was 1750±140 pS (n=4). The single channel currents were decorated with brief current fluctuations (mean lifetime, 0.15±0.07 ms; amplitude, 140 1 42 pS; frequency of occurrence, 8.6±1.5 $s^{-1}$, n=3). Due to their short lifetimes, some current spikes were not completely resolved at the filter frequency of 10 kHz. As this study focuses on the sequence-specific binding events, the current spikes, which presumably represent translocation events were not investigated further; FIG. 7A-1).

B. Results

The conductance of $H_6$(17C-oligo-A), is lower than the value for $H_7$ channels (1950±100 pS, n=3) or $H_6$(17C-oligo-A), channels, which had been treated with DTT to cleave the disulfide bond between the oligonucleotide and αHL (1900±110 pS, n=3). The reduced conductance of $H_6$(17C-oligo-A), indicates that the tethered DNA-oligonucleotide partly blocks the current flowing through the nanopore (FIG. 7A-2).

When 67 nM oligo-B (3'-GTAAGTGG-5'; SEQ ID NO:2), with a sequence fully complementary to the tethered oligo-A (5'-CATTCACC-3'; SEQ ID NO:1), was added to the cis side of the bilayer two type of events occurred: negative current deflections (FIG. 7B-1, symbol b) characterized by a duration of hundreds of milliseconds, a mean amplitude of 605±31 pS and a frequency of occurrence of 0.48±0.08 s$^{-1}$ (n=4); and spike-like events (FIG. 7B-1, symbol s) with a mean lifetime of 0.3±0.1 ms, a mean amplitude of 590±120 pS and a frequency of occurrence of 0.13±0.02 s$^{-1}$ (n=4).

The current deflections (b) most likely represent single oligo-B molecules, which enter the DNA-nanopore 5'-end first and form a duplex with the tethered, complementary oligo-A. The spike at the end of the binding event (FIG. 7B-1) indicates that after dissociation oligo-A passes the inner constriction to exit on the trans side of the pore (FIG. 7B-2). The spikes (s) probably arise from oligo-B strands, which enter the DNA-nanopore with the 3'-end first, leaving them unable to form a duplex with the tethered oligonucleotide. Alternatively, spikes (s) could also stem from oligo-B strands, which enter the pore with the 5'-end first but do not bind.

To prove that the current deflections (b) represented oligo-B binding to the tethered oligo-A, excess free oligo-A was added on the cis side. If the binding were specific, excess oligo-A would compete for the binding of oligo-B to tethered oligo-A (FIG. 7C-2). Indeed, the frequency of occurrence of the proposed binding events was reduced 21-fold (0.02 s$^{-1}$), while spikes, now presumably stemming from oligo-B transiting the lumen without binding, appeared with a frequency of occurrence 5.2 s$^{-1}$ (FIG. 7C-1).

Figure 8A:
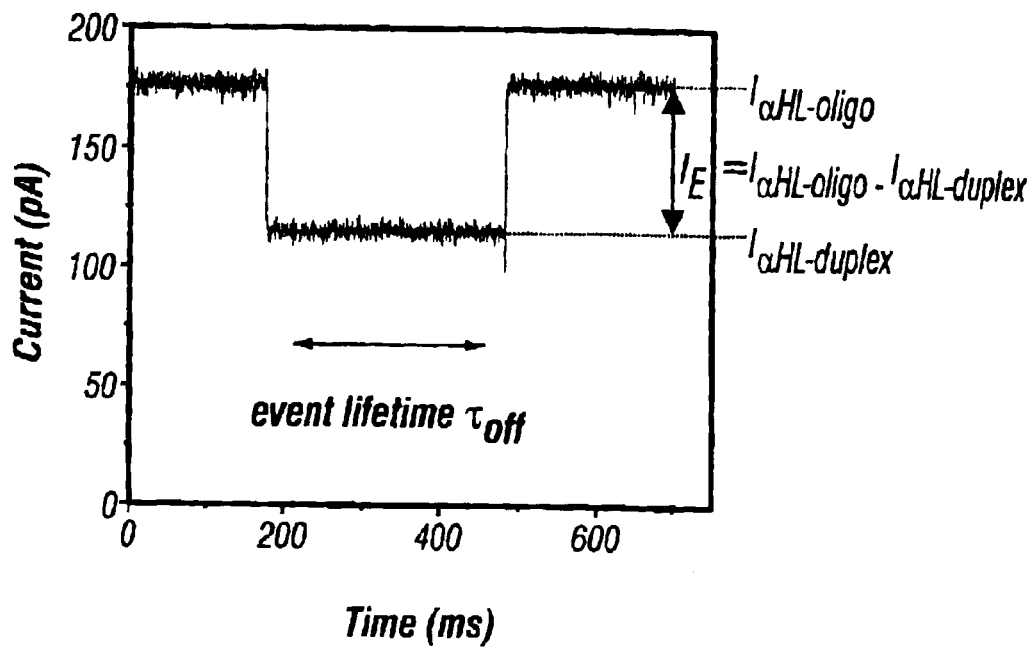
FIG. 8A and FIG. 8B. Statistical summary of the binding events of DNA oligonucleotides oligo-B to $H_6$(17C-oligo-A)$_1$.
Figure 8B:
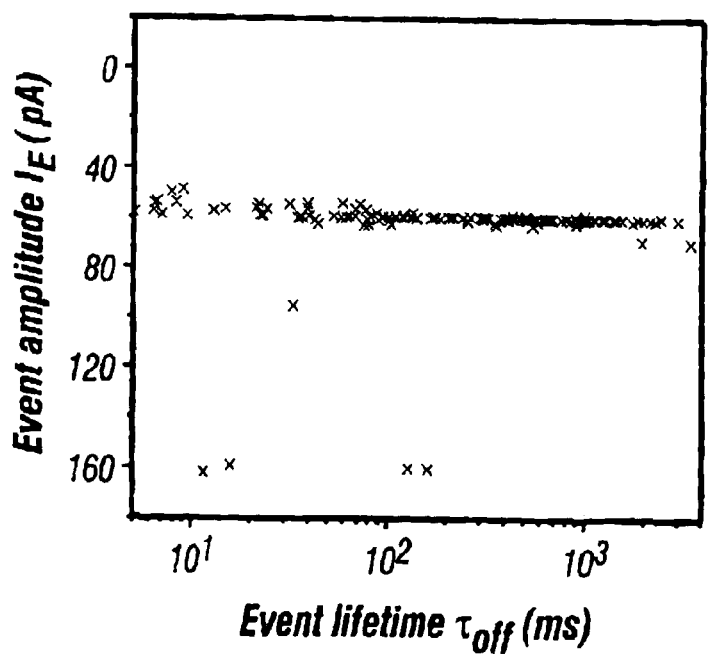

Single channel current recording was used to derive the kinetic constants for the association and the dissociation of individual DNA strands. Each binding event, oligo-B to $H_6$(17C-oligo-A), (FIG. 7B-1), was characterized by its event amplitude $I_E$ and its event lifetime $\tau_{off}$ (FIG. 8A). The two characteristic parameters for hundreds of individual events from one recording were plotted onto an event diagram, in which each point represents one event (FIG. 8B).

While the event amplitudes were narrowly distributed (597±20 pS), the event lifetimes were scattered between 50 and 2000 ms with a mean value of 470±400 ms. Lifetime histogram analysis of four recordings with a total number of 4000 events revealed that the event population was composed of two different event types with $\tau_{off}$ values of 119±23 ms (20±3% of the events) and 620±63 ms (80±3%). Fitting the kinetic parameters to different kinetic schemes revealed, that the two event types represent two classes of binding events with different stability constants: $K_{d-1}$=9.3×10$^{-6}$, $K_{d-}$=4.5×10$^{-7}$.

In more detail, the kinetic scheme for DNA duplex formation and dissociation in the internal cavity of αHL is as follows:

Single channel current analysis revealed two $\tau_{off}$ and proportion (P) values for the dissociation of oligo-B (5'-GGTGAATG-3'; SEQ ID NO:2) from the tethered DNA strand oligo-A (5'-CATTCACC-3'): $\tau_{off-1}$=119±23 ms, $P_1$ 32 20±3% of the events; $\tau_{off-2}$=620±63 ms, $P_2$=80±3%.

To account for the values, two simple kinetic models can be envisioned.

Model I

In this model, DNA duplex AB forms by the association of DNA strands A and B and is assumed to dissociate along two kinetically different routes characterized by the rate constants $k_{off-1}$ and $k_{off-2}$. In accordance, the overall rate of duplex dissociation is:

$$v_{off}=(k_{off-1}+k_{off-2})\cdot[AB]$$

The probability for duplex AB to dissociate along route 1 would is given by:

$$P_1=k_{off-1}/(k_{off-1}+k_{off-2})=\tau_{off-2}/(\tau_{off-1}+\tau_{off-2})$$

The experimentally derived values of $\tau_{off-1}$=119 ms and $\tau_{off-2}$=620 ms, yields $\tau_{off-2}/(\tau_{off-1}+\tau_{off-2})$=0.84. But, the experimental value for $P_1$ is 0.2. Therefore, the observed kinetic parameters can not be explained by the kinetic model I. More likely, hybridization follows kinetic model II, characterized by two completely separate binding events:

Model II

The total rate of strand association in this model is:

$$i\ v_{on}=k_{on}\cdot[A]\cdot[B]=(k_{on-1}+k_{on-2})\cdot[A]\cdot[B]$$

The individual rate constants for duplex formation and dissociation and the stability constants are:

$$k_{on-1}=P_1\cdot k_{on} \qquad k_{on-2}=P_2\cdot k_{on}$$
$$k_{off-1}=1/\tau_{off-1} \qquad k_{off-2}=1/\tau_{off-2}$$
$$K_{d-1}=k_{off-1}/k_{on-1} \qquad K_{d-2}=k_{off-2}/k_{on-2}$$

Inserting the values for $P_1$=0.2, $P_2$=0.8, $k_{on}$=4.5×10$^6$ M$^{-1}$ s$^{-1}$, $\tau_{off-1}$=119 ms and $\tau_{off-2}$=620 ms gives $$k_{on-1}=9\times10^5\ M^{-1}s^{-1} \qquad k_{on-2}=3.6\times10^6\ M^{-1}s^{-1}$$
$$k_{off-1}=8.4\ s^{-1} \qquad k_{off-2}=1.6\ s^{-1}$$
$$K_{d-1}=9.3\times10^{-6} \qquad K_{d-2}=4.5\times10^{-7}$$

While it would be interesting to further investigate the nature of the two different binding events, it is clear that $K_{d-2}$ dominates the composite $K_d$ obtained from the mean lifetime, $\tau_{off}$. Therefore, to simplify the analysis, composite kinetic constants are used here. The inter-event intervals ($\tau_{on}$) showed a linear dependence on the concentration of oligo-B in the examined range (5 to 400 nM). Through the analysis of the inter-event intervals ($\tau_{on}$) and the event lifetimes ($\tau_{off}$) of three independent single channel current recordings, it was possible to obtain the kinetic constants for strand association ($k_{on}$) and strand dissociation ($k_{off}$).

The association constant ($k_{on}$) for duplex formation was calculated from $k_{on}=1/(c \times \tau_{on})$, where $\tau_{on}$ is the inter-event interval and c the concentration of oligo-B in the cis chamber. The strand dissociation constant ($k_{off}$) was derived from the event lifetime ($\tau_{off}$): $k_{off}=1/\tau_{off}$ (Moczydlowski, 1986).

The value of $k_{on}$ was $4.5 \times 10^6$ M$^{-1}$ s$^{-1}$ and $k_{off}$ was 1.9 s$^{-1}$. The value of $k_{on}$ falls within the range of values usually observed for strand association in homogeneous solution (Braunlin and Bloomfield, 1991; Porschke and Eigen, 1971; Cantor and Schimmel, 1980; Riesner and Romer, 1973); and $k_{off}$ is slightly higher than the calculated value for dissociation in solution (0.6 s$^{-1}$). The rate constant for duplex dissociation, $k_{off}$, in homogeneous solution was calculated using the relation $k_{off}=k_{on} \times K_d$. Given that the association rate constant $k_{on}$ is usually not strongly dependent on the length and type of oligonucleotide (Cantor and Schimmel, 1980), a value of $10^6$ M$^{-1}$ s$^{-1}$ was assumed for $k_{on}$. The dissociation equilibrium constant $K_d$ was derived from thermodynamic data (Martin et al., 1971).

It might be concluded that the kinetics of duplex formation in a nanopore are very similar to duplex formation in homogeneous solution. Alternatively, the kinetics might be affected by opposing but compensating factors; for example, sterical constraints or effects of the applied potential (Gilles et al., 1999). Hence, single channel current studies with a DNA-nanopore give kinetic data consistent with established literature values and, in addition, offer the ability to detect properties (e.g., complex kinetics) often difficult to investigate by conventional methods which measure bulk properties.

As mismatched bases are known to weaken duplex formation between DNA strands (Aboul-ela et al., 1985), the inventors tested whether a DNA-nanopore could discriminate between DNA molecules differing by a single base. A common point mutation in the reverse transcriptase gene of HIV was examined, which confers resistance to the widely used antiviral drug nevirapine (Hanna et al., 2000; Richman et al., 1994).

The tethered oligonucleotide with a length of 8 nt (5'-TGACAGAT-3'; SEQ ID NO:3) was fully complementary to an 8 nt portion of a 30 nt coding fragment from the drug-resistant virus strain (FIG. 9, oligo-181C; SEQ ID NO:5), while the wild type (wt) virus (FIG. 9, oligo-181Y; SEQ ID NO:4) included a single mismatch. DNA strands oligo-181C and oligo-Y can be derived from HIV RNA by RT-PCR™ of the reverse transcriptase gene, followed by digestion with restriction enzyme NlaIII (with the recognition sequence and cleavage site CATG|) and linear PCR™ with a primer of the sequence 5'-ACAAAATCCAGA-3' (nucleotides 1 through 12 of SEQ ID NO:4 and SEQ ID NO:5).

Figure 9:
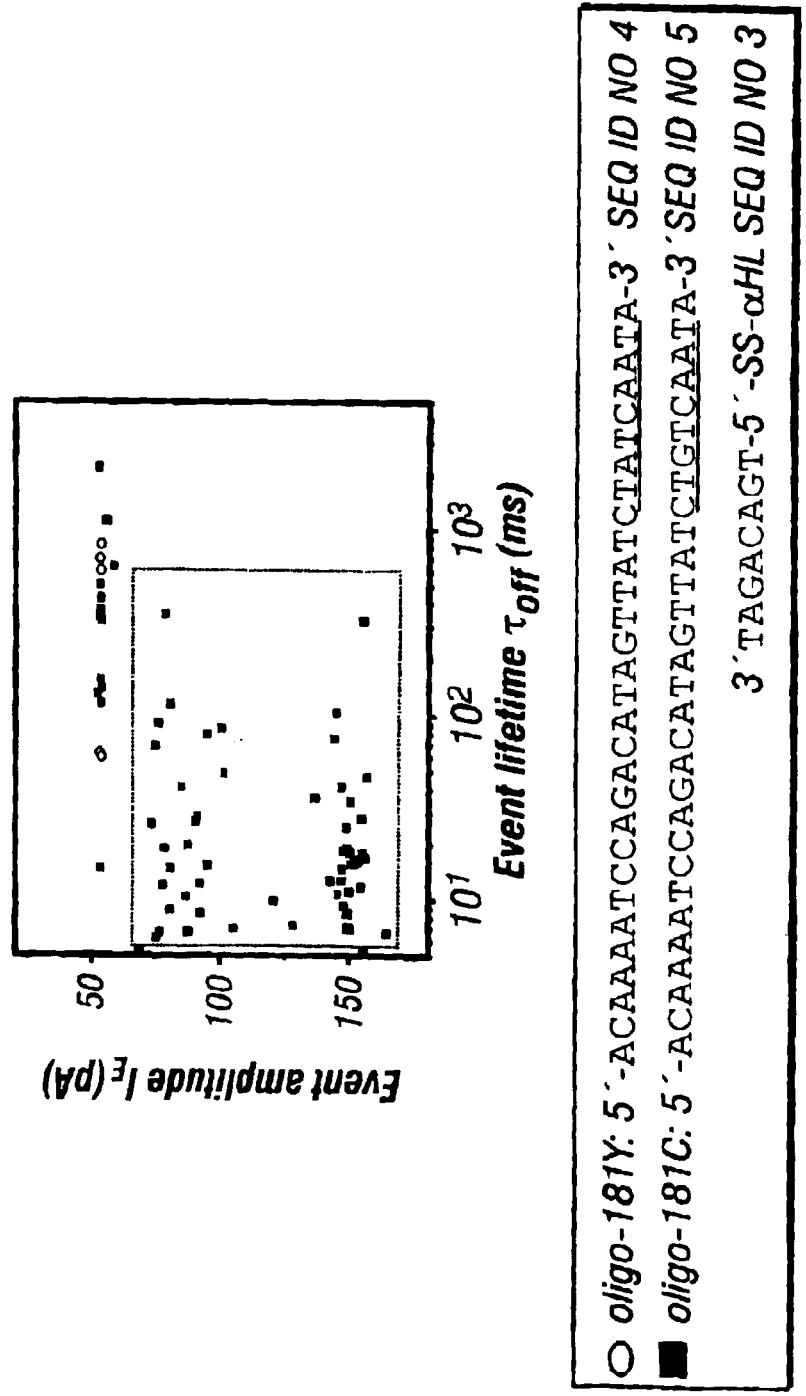
FIG. 9. A DNA-nanopore detects a common mutation, which confers resistance to the drug nevirapine in the reverse transcriptase gene of HIV. The event diagram shows the event lifetime, $\tau_{off}$, and event amplitude, $I_E$, for two HIV-derived 30-nt DNA strands, oligo-181C and oligo-181Y, interacting with $H_6$(17C-5'-TGACAGAT-3' (SEQ ID NO:3))$_1$. Oligo-181C (SEQ ID NO:5) carries the drug resistance mutation and forms a 8 bp duplex with the tethered oligonucleotide, whereas the wild type oligo-181Y (SEQ ID NO:4) forms a duplex with a single base mismatch. The dashed box indicates an event window populated only by 181C binding events. The event diagram displays data from one current recording for each of oligo-181C and oligo-181Y. The DNA strand concentration was 670 nM and the recordings were 5 min in duration. The study was repeated and gave the same result.

When wt oligo-181Y was added to the cis chamber, five events with an event lifetime longer than the cut-off of 5 ms were recorded in 300 s (FIG. 9; open circles). By contrast, in the same time period, mutant oligo-181C gave rise to 70 events with event amplitudes ($I_E$) greater than those found for the five events with oligo-181Y (FIG. 9, filled squares). This indicates that the oligo-181C strands, when bound to the tethered oligonucleotide, thread into the transmembrane barrel through the central constriction producing a strong block (Movileanu et al., 2000; compare with the block caused by shorter oligos in FIG. 7A-1, FIG. 7B-1 and FIG. 7C-1 with FIG. 8A and FIG. 8B).

Because 181C events populated a distinct area in the event diagram, a 181C-specific event window (FIG. 9, box) useful for the assignment of new events was defined. Any new event falling into the window can be identified as stemming from a single strand of 181C (no 181Y events, but one hundred and fifty 181C events, fell in the box during two recordings). This study shows that the DNA-nanopore was able to discriminate, on the single molecule level, between two 30 nt-long ssDNA strands differing only by a single base. Hence, DNA-nanopores represent novel biosensor elements for the ultrasensitive detection of DNA from medically or environmentally important samples.

A DNA-nanopore was also used to sequence a codon on a single strand of DNA. The sequencing principle was based on the match/mismatch-dependent binding time of hybridized oligonucleotides (Table 6A). In the following description, the unknown nucleotides (indicated by X and Z of defined designations in the described oligonucleotides) are also represented as "N" in the appended sequence listing.

A ssDNA oligonucleotide (5'-GCATTCX$_1$X$_2$X$_3$-3'; SEQ ID NO:6) with three unknown bases (X$_1$, X$_2$, X$_3$) was tethered to Cys$^{17}$ of αHL. To identify the first base X$_1$, four oligonucleotides with sequences 3'-CGTAAGZ$_1$-5' (SEQ ID NO:7; Z$_1$=A, C, G, T) were used and their interactions with the tethered DNA strand analyzed by single channel current recording. Of the four oligonucleotides, one was characterized by a higher average event lifetime compared with the other three oligonucleotides (Table 6A). Therefore, this oligonucleotide, carrying a T in position Z, was fully complementary to the tethered DNA strand, and hence, the base X$_1$ was defined to be A. To identify the other two bases (X$_2$, X$_3$), two additional rounds were performed, each with a different set of oligonucleotides (3'-GTAAGTZ$_2$-5', SEQ ID NO:8 and 3'-TAAGTGZ$_3$-5', SEQ ID NO:9; Table 6A). Sequence information obtained in one round was used to design the oligonucleotides for the next round. In this way, the codon X$_1$X$_2$X$_3$ was unambiguously deduced to be ACC (Table 6A).

The success of this method of sequencing depends on the differences in the match/mismatch-dependent event lifetimes. Therefore, the influence of the position of the mismatch on the lifetime was analyzed using the oligonucleotides: 5'-ATTCACC-3' (SEQ ID NO:10); 3'-TAAZ$_4$TGG-5' (SEQ ID NO:11) and 3'-TAZ$_5$GTGG-5' (SEQ ID NO:12). It was found that the mismatch had the most dramatic effect when it was positioned in the middle of the oligonucleotide (Table 6B). For two different internal positions, the event lifetimes for mismatched oligonucleotides were 8- and 60-times shorter than those of the completely complementary oligonucleotide (Table 6B). By contrast, the event lifetimes for three oligonucleotides with different terminal mismatches were 2.3, 5.9 and 4.7 shorter than the lifetimes of the corresponding complementary oligonucleotides (Table 6A).

The sequencing of tethered DNA using the present hybridization-based method, would require molecular biological and chemical manipulations such as linear PCR™ with 5'-thiol-modified primers and chemical attachment of the DNA-strand to the nanopore. Clearly, time-consuming manipulations could be greatly reduced if copies of a non-tethered DNA strand were sequenced with an array of DNA-nanopores modified with oligonucleotides of known sequence. The viability of this approach was proven for the determination of a single base (Table 6C).

Oligonucleotide 6 (3'-GTAAGTX$_6$G-5'; SEQ ID NO:14) with the unknown base X$_6$ was added to the cis side of four different αHL pores, which had been modified with 5'-CATTCAZ$_6$-3' (SEQ ID NO:13; Z$_6$=A, C, G, T), and analyzed by single channel current recording. The average lifetime of binding events with αHL-oligonucleotides wherein Z$_6$=G was longer than the values for the other three DNA-nanopores (Table 6C), and the unknown base $X_6$ was deduced to be C.

TABLE 6A event lifetimes $\tau_{off}$ [ms] for oligos 1, 2 and 3
interacting with αHL-SS-5'-GCATTCX$_1$X$_2$X$_3$-3'
(SEQ ID NO:6)

| αHL-SS-5'-GCATTCX$_1$X$_2$X$_3$-3' (SEQ ID NO:6) | | | | | | | |
|---|---|---|---|---|---|---|---|
| | | | $Z_n$ | | | | |
| Interacting with | A | C | G | T | $Z_n$ | | $X_n$ |
| oligo-1 3'-CGTAAGZ$_1$-5' (SEQ ID NO:7) | → 6.7 | 8.2 | 7.9 | 19 | T | → | A |
| oligo-2 3'-GTAAGTZ$_2$-5' (SEQ ID NO:8) | → 1.7 | 1.5 | 10 | 1.6 | G | → | C |
| oligo-3 3'-TAAGTGZ$_3$-5' (SEQ ID NO:9) | → 5.3 | 3.9 | 25 | 4.0 | G | → | C |
| | | | | | | | codon ACC |

TABLE 6B event lifetimes $\tau_{off}$ [ms] for oligos 4 and 5
interacting with αHL-SS-5'-ATTCACC-3'
(SEQ ID NO:10)

| αHL-SS-5'-ATTCACC-3' (SEQ ID NO:10) | | | | |
|---|---|---|---|---|
| | | | $Z_n$ | |
| Interacting with | A | C | G | T |
| oligo-4 3'-TAAZ$_4$TGG-5' (SEQ ID NO:11) | → <0.5 | <0.5 | 29 | <0.5 |
| oligo-5 3'-TAZ$_5$GTGG-5' (SEQ ID NO:12) | → 29 | <0.5 | 3.5 | 1.6 |

TABLE 6C event lifetimes $\tau_{off}$ [ms] for oligo 6
interacting with αHL-SS-5'-CATTCAZ$_6$-3'
(SEQ ID NO:13)

| oligo 6 3'-GTAAGTX$_6$G-5' (SEQ ID NO:14) | | | | | | | |
|---|---|---|---|---|---|---|---|
| | | | | | $Z_n$ | | |
| Interacting with | A | C | G | T | $Z_6$ | | $X_6$ |
| αHL-SS-5'-CATTCAZ$_6$-3' (SEQ ID NO:13) | → 1.1 | 13 | 2.0 | 1.6 | → C | → | G |

Table 6A, Table 6B and Table 6C: Single base mismatches influence the binding time of individual DNA strands to a DNA-nanopore. Table 6A.

Sequencing of a codon in an individual ssDNA molecule tethered to the αHL pore. The sequence was determined by the match/mismatch-dependent binding time of hybridizing oligonucleotides. Table 6B. The position of a single base mismatch in an oligonucleotide interacting with a DNA-nanopore strongly influences the event lifetime $\tau_{off}$. Table 6C. Hybridization-based determination of an unknown base in non-tethered ssDNA by using an "array" of four DNA-nanopores with known sequence. The values in A, B, C are the arithmetic means of the lifetimes $\tau_{off}$ of one single channel current recording. All studies were repeated and gave similar values. The concentration of oligonucleotides in the cis chamber was 200 nM, and events were counted if 400 pS ≤ $I_E$ ≤ 700 pS and $\tau_{off}$ ≥ 0.5 ms. Each recording had a duration of 4 min and the number of events in a recording ranged from 400 to 1600.

The use of this strategy to sequence a target gene would require multiple ssDNA copies with lengths between seven and 20 nt. In one approach, these fragments could be obtained by PCR™ amplification, followed by selective enzymatic degradation of the template strands and fragmentation of the product strands. The protocol includes pre-amplification of the desired PCR™-product using the nucleotide UTP instead of TTP, followed by linear PCR™ in the presence of TTP and UTP to yield product strands containing TTP and UTP at random positions. The degradation of the template strands containing UTP and the fragmentation of the product strands to ssDNA oligonucleotides is accomplished by the enzymes uracil DNA-glycosylase and E. coli endonuclease IV. If necessary, the DNA fragments can be partially purified.

Alternatively, short fragments can be generated by using restriction endonucleases with a 2 bp recognition sequence. Chlorella virus-encoded restriction endonucleases have short (2 to 4 bp) recognition sites. For example, the enzyme CviTI cuts at the site (NG|CN). Additional information is available at www.cvienzymes.com.

In summary, αHL pores modified with a single DNA oligonucleotide have been used to study duplex formation by individual DNA molecules, thus extending the proof of principle for the present invention. The DNA-nanopores can be used in at least two different modes. In the first mode, a single DNA strand is tethered to the pore and analyzed by the binding of partly or completely complementary oligonucleotides. In the second mode, a solution of free analyte DNA is added to the cis chamber and analyzed with DNA-nanopores of known sequence.

Using DNA-nanopores operating in the first mode, the kinetics of DNA duplex formation was studied at the single molecule level, thereby avoiding problems of conventional techniques such as surface plasmon resonance (SPR). In SPR, the transport of the analyte to the sensor surface can be impeded by slow diffusion through the immobilization matrix (Schuck, 1997). Indeed, $k_{on}$ values derived by SPR are reported to be one to two orders of magnitude lower (Jensen et al., 1997; Gotoh et al., 1995) than the values for duplex formation in solution (Braunlin and Bloomfield, 1991; Porschke and Eigen, 1971; Cantor and Schimmel, 1980; Riesner and Romer, 1973). In comparison, the present invention yields kinetic constants in excellent agreement with experimentally-derived data for duplex formation in solution. Furthermore, the use of DNA-nanopores provides kinetic parameters not readily obtained by conventional techniques, which measure bulk properties. For example, two different binding events were observed characterized by their $k_{on}$, $k_{off}$ and $K_d$ values.

DNA-nanopores operating in the first mode can also be used to sequence an individual tethered DNA strand as shown for a complete codon in the present study. In the current configuration, at least one codon can be determined per attached DNA strand; hence, sequencing of a 1000 bp gene would require at least 334 chemically modified αHL pores. Therefore, the utility of DNA-nanopores for sequencing will be improved by miniaturization of single channel current recordings to allow the simultaneous and automated analysis of hundreds of different channels.

To produce microfabricated chip-based channel arrays, the single channels should be maintained in stabilized membranes and individual channels should be electronically addressed within an array of hundreds of channels. Improving the stability of membranes is achieved using supported bilayers (Cornell et al., 1997; Sotra et al., 1999) and nanoscale apertures in a variety of materials (Hulteen et al., 1998). Electronically addressing individual channels within an array of hundreds of channels is achieved using microfabrication expertise (Quake and Scherer, 2000) and the production of chip-based circuits. Sequencing of single DNA strands using the first mode would require fragments of each target DNA strand to be covalently attached to a nanopore. Under optimized conditions for chemical tethering of the DNA strands, the detection limit would lie at a few copies of a target strand.

Using the second mode, non-tethered target DNA strands could be sequenced by arrays of nanopores modified with known DNA sequences. In contrast to the first mode, this configuration would allow re-use of the arrays. The viability of this strategy was shown for the identification of a base with an "array" of four DNA-pores. A particularly preferred application of arrays of DNA-pores operating in the second mode lies in the sequencing of variants of a known gene, such as the protease gene of drug-resistant HIV strains, or the diagnostic screening of single nucleotide polymorphisms (SNPs) in human genes. In order to identify single point mutations in a 400 bp-gene, 400×4=1600 DNA-pores with different DNA 7mers would be sufficient. The use of arrays of DNA-pores will likely also offer advantages.

The current detection limit of this system in terms of final target DNA concentration is 1 nM. To decrease the detection limit and fully capitalize on the high sensitivity of DNA-nanopores, the sample volume can be reduced by the miniaturization of the chamber reservoir. Assuming a sample volume of one nL, a detection limit of one attomole can be achieved. The transport of a sample volume of a few nL is readily done with state-of-the-art fluidic systems (Quake and Scherer, 2000). To further reduce the detection limit, the target DNA can be electrophoretically transported and concentrated on the biosensor surface (Gilles et al., 1999). Furthermore, the recording time for DNA-nanopores is a few minutes, while the time required for the hybridization and read out of DNA-chips is 45 to 60 minutes (Hegde et al., 2000).

DNA-nanopores can also improve the prospects for DNA sequencing by translocation. This approach assumes that individual bases can be identified by their characteristic channel blockades and/or dwell times as a single DNA strand moves through a nanopore (Akeson et al., 1999; Meller et al., 2000). DNA homo- or block polymers 100 nt in length and with different base compositions have been identified by their characteristic signatures (Akeson et al., 1999; Meller et al., 2000). Single base resolution has been elusive, because the DNA strands translocate too quickly through the nanopore to allow the identification of single bases (for example 190 $\mu$s for $(dA)_{100}$=1.9 ps per nt). To improve the resolution, the translocating DNA strand should be slowed down. The DNA-nanopores of the present invention represent an important advance here, because the tethered DNA strand provides a physical constriction and the chemical "stickyness" necessary to retard the translocating DNA strand. In addition, the bases of the tethered DNA can selectively interact with bases of the translocating DNA and thereby cause base-specific differences in the dwell-times and/or current blockades.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aboul-ela, Koh, Tinoco Jr., Martin, *Nucleic Acids Res.,* 13:4811, 1985.

Akeson, Branton, Kasianowicz, Brandin, Deamer, "Microsecond time-scale discrimination among polycytidylic acid, polyadenylic acid and polyuridylic acid as homopolymers or as segments within single RNA molecules," *Biophys. J,* 77:3227–3233, 1999.

Andersen, *Biophys J.,* 77:2899, 1999.

Baumann et al., *Biophys J.,* 78:1965, 2000.

Bayley, *Curr. Op. Biotechnol.,* 10:94–103, 1999.

Bezrukov and Kasianowicz, *Eur. Biophys. J.,* 26:471–476, 1997.

Bezrukov and Vodyanoy, *Biophys. J.,* 64:16–25, 1993.

Bezrukov, Vodyanoy, Parsegian, "Counting polymers moving through a single ion channel," *Nature,* 370:279–281, 1994.

Bezrukov, Vodyanoy, Brutyan, Kasianowicz, "Dynamics and free energy of polymer partitioning into a nanoscale pore," *Macromolecules,* 29:8517–8522, 1996.

Braha, et al., "Designed protein pores as components for biosensors," *Chem. Biol.,* 4:497–505, 1997.

Braunlin and Bloomfield, *Biochemistry,* 30:754, 1991.

Cantor and Schimmel, *Biophysical Chemistry, Part III, The behavior of biological macromolecules,* W. H. Freeman and Co., New York, 1980.

Chang, Niblack, Walker, Bayley, "A photogenerated pore-forming protein," *Chem. Biol.,* 2:391–400, 1995.

Cheley, Braha, Lu, Conlan, Bayley, "A functional protein pore with a "retro" transmembrane domain," *Protein Sci.,* 8:1257–1267, 1999.

Chilkoti, Tan, Stayton, "Site-directed mutagenesis studies of the high-affinity streptavidin-biotin complex: contributions of tryptophan residues 79, 108, and 120," *Proc. Natl. Acad. Sci. USA,* 92:1754–1758, 1995a.

Chilkoti, Boland, Ratner, Stayton, "The relationship between ligand-binding thermodynamics and protein-ligand interaction forces measured by atomic force microscopy," *Biophys. J,* 69:2125–2130, 1995b.

Chlorella virus-encoded restriction endonucleases have short (2 to 4 bp) recognition sites.

For example, the enzyme CviTI cuts at the site (NG|CN). Additional information is available at www.cvienzymes.com.

Christopher, "SPOCK: the structural properties observation and calculation kit (program manual). Center for Macromolecular Design, Texas A&M University, College Station, Tex., 1998.

Corey et al., *Bioconjug Chem.,* 6:93, 1995.

Cornell et al, *Nature,* 387:580, 1997.

Deamer and Akeson, *Trends Biotechnol.,* 18:147, 2000.

Ding, Long, Hayashi, Bulmus, Hoffman, Stayton, *Bioconjugate Chem.,* 10:395–400, 1999.

Doi, *Introduction to polymer physics*; Clarendon Press. 1996.

Eigen and Rigler, *Proc. Natl. Acad. Sci. USA,* 91:5740, 1994.

Fussle, Bhakdi, Sziegoleit, Tranum-Jensen, Kranz, Wellensiek, *J. Cell Biol.*, 91:83–94, 1981.

Gilles, Wu, Foster, Dillon, Chanock, *Nat. Biotechnol.*, 17:365, 1999.

Gimzewski and Joachim, *Science*, 283:1683–1688, 1999.

Gotoh, Hasegawa, Shinohara, Shimizu, Tosu, *DNA Res.*, 2:285, 1995.

Gouaux, "α-Hemolysin from Staphylococcus aureus: an archetype of β-barrel, channel-forming toxins," *J. Struct. Biol.*, 121:110–122, 1998.

Gu, Braha, Conlan, Cheley, Bayley, "Stochastic sensing of organic analytes by a pore-forming protein containing a molecular adapter," *Nature*, 398:686–690, 1999.

Ha, Ting, Liang, Caldwell, Deniz, Chemla, Schultz, Weiss, *Proc. Natl. Acad. Sci. USA*, 96:893–898, 1999.

Hanna et al., *J. Infect. Dis.*, 181:904, 2000.

Hegde et al., *Biotechniques*, 29:548, 2000.

Henrickson, Misakian, Robertson, Kasianowicz, *Phys. Rev. Lett.*, 85:3057, 2000.

Hladky and Haydon, *Nature*, 225:451–453, 1970.

Hoffman, *Macromol. Symp.*, 98:645–664, 1995.

Howorka and Bayley, *BioTechniques*, 25:764, 1998.

Howorka et al., *J. Am. Chem. Soc.*, 122:2411, 2000.

Hubbell, *Curr. Op. Biotechnol.*, 10:123–129, 1999.

Hulteen, Jirage, Martin, *J. Amer. Chem. Soc.*, 120:6603, 1998.

Jensen, Orum, Nielsen, Norden, *Biochemistry*, 36:5072, 1997.

Kasianowicz, Brandin, Branton, Deamer, "Characterization of individual polynucleotide molecules using a membrane channel," *Proc. Natl. Acad. Sci. USA*, 93:13770–13773, 1996.

Kay, *Nature Struct. Biol.*, 5:145–152, 1998.

Kenworthy, Hristova, Needham, McIntosh, *Biophys. J*, 68:1921–1936, 1995.

Kinjo, Nishimura, Koyama, Mets, Rigler, *Anal. Biochem.*, 260:166, 1998.

Krasilnikov, Sabirov, Ternovsky, Merzliak, Muratkhodjaev, *FEMS Microbiol. Immunol.*, 105:93–100, 1992.

Lipshutz, Fodor, Gingeras, Lockhart, *Nat. Genet.*, 21:20, 1999.

Lu, Xun, Xie, *Science*, 282:1877–1882, 1998.

Mao, Sun, Shen, Seeman, "A nanomechanical device based on the B-Z transition of DNA," *Nature*, 397:144–146, 1999.

Marszalek et al., "Mechanical unfolding intermediates in titin molecules," *Nature*, 402:100–103, 1999.

Martin et al., *J. Mol. Biol.*, 57:201, 1971.

Mehta, Rief, Spudich, Smith, Simmons, "Single-molecule biomechanics with optical methods," *Science*, 283:1689–1695, 1999.

Meller, Nivon, Brandin, Golovchenko, Branton, *Proc. Natl. Acad. Sci. USA*, 97:1079, 2000.

Menestrina, *Membrane Biol.*, 90:177–190, 1986.

Merzlyak et al., "Polymeric nonelectrolytes to probe pore geometry: application to the α-toxin transmembrane channel," *Biophys. J.*, 77:3023–3033, 1999.

Moczydlowski, In: *Ion channel reconstitution* C. Miller, (ed.), Plenum Press, New York, pp. 75, 1986.

Moerner and Orrit, *Science*, 283:1670–1676, 1999.

Montal and Mueller, "P. Formation of bimolecular membranes from lipid monolayers and study of their electrical properties," *Proc. Natl. Acad. Sci. USA*, 69:3561–3566, 1972.

Movileanu, Howorka, Braha, Bayley, *Nat. Biotechnol.*, 18:1091, 2000.

Olson, Nariya, Yokota, Kamio, Gouaux, *Nature Struct. Biol.*, 6:134–140, 1999.

Panchal, Cusack, Cheley, Bayley, "Tumor protease-activated, pore-forming toxins from a combinatorial library," *Nature Biotechnology*, 14:852–856, 1996.

Perez-Luna et al., "Molecular recognition between genetically engineered streptavidin and surface-bound biotin," *J. Am. Chem. Soc.*,121:6469–6478, 1999.

Porschke and Eigen, *J. Mol. Biol.*, 62:361, 1971.

Quake and Scherer, *Science*, 290:1536, 2000.

Richman et al., *J. Virol.*, 68:1660, 1994.

Riesner and Romer, In: *Physico-chemical properties of nucleic acids*, J. Duchesne, (ed.) Academic Press, New York, vol. 2, pp. 237, 1973.

Rex, Zuckermann, Lafleur, Silvius, *Biophys. J*, 75:2900–2914, 1998.

Russo, Bayley, Toner, "Reversible permeabilization of plasma membranes with an engineered switchable pore," *Nature Biotechnology*, 15:278–282, 1997.

Sakmann and Neher, *Single-channel recording*; Plenum: New York, 1995.

Sano and Cantor, "Intersubunit contacts made by tryptophan 120 with biotin are essential for both strong biotin binding and biotin-induced tighter subunit association of streptavidin," *Proc. Natl. Acad Sci. USA*, 92:3180–3184, 1995.

Scherrer and Gerhardt, *Bacteriol.*, 1971, 107:718–735, 1971.

Schuck, *Annu. Rev. Biophys. Biomol. Struct.*, 26:541, 1997.

Sheth and Leckband, *Proc. Natl. Acad Sci. USA*, 94:8399–8404, 1997.

Slatin, Qiu, Jakes, Finkelstein, "Identification of a translocated protein segment in a voltage-dependent channel," *Nature*, 371:158–161, 1994.

Smith, Cui, Bustamante, *Science*, 271:795, 1996.

Song et al., "Structure of staphylococcal α-hemolysin, a heptameric transmembrane pore," *Science*, 274:1859–1865, 1996.

Stayton et al., "Control of protein-ligand recognition using a stimuli-responsive polymer," *Nature*, 378:472–474, 1995.

Stora, Lakey, Vogel, *Angew Chem. Int. Ed.*, 38:389, 1999.

Strunz, Oroszlan, Schafer, Guntherodt, *Proc. Natl. Acad. Sci. USA*, 96:11277, 1999.

Tan and Yeung, *Anal. Chem.*, 69:4242–4248, 1997.

Taton, Mirkin, Letsinger, *Science*, 289:1757, 2000.

Urry, *Biopolymers*, 47:167–178, 1998.

Walker and Bayley, "A pore-forming protein with a protease-activated trigger," *Protein Eng.*, 7:91–97, 1994.

Walker and Bayley, "Key residues for membrane binding, oligomerization, and pore-forming activity of staphylococcal α-hemolysin identified by cysteine scanning mutagenesis and targeted chemical modification," *J. Biol. Chem.*, 270:23065–23071, 1995a.

Walker and Bayley, "Restoration of pore-forming activity in staphylococcal a.-hemolysin by targeted chemical modification," *Protein Eng.*, 8:491–495, 1995b.

Walker, Krishnasastry, Zorn, Kasianowicz, Bayley, "Functional expression of the α-hemolysin of *Staphylococcus aureus* in intact *Escherichia coli* and in cell lysates," *J. Biol. Chem.*, 267:10902–10909, 1992a.

Walker, Krishnasastry, Zorn, Bayley, *J. Biol. Chem.*, 267:21782–21786, 1992b.

Walker, Krishnasastry, Bayley, *J. Biol. Chem.*, 268:5285–5292, 1993.

Walker, Braha, Cheley, Bayley, *Chem. Biol.*, 1995, 2:99–105, 1995.

Weiss, "Fluorescence spectroscopy of single biomolecules," *Science*, 283:1676–1683, 1999.

Wong, Kuhl, Israelachvili, Mullah, Zalipsky, *Science*, 275:820–822, 1997.

Xie and Lu, "Single-molecule enzymology," *J. Biol. Chem.*, 274:15967–15970, 1999.

Xue and Yeung, *Nature*, 373:681–683, 1995.

Ziegler and Göpel, *Curr. Op. Chem. Biol.*, 2:585–591, 1998.

What is claimed is:

1. A method of detecting the presence of an analyte in a sample, the method comprising:

contacting said sample with a pore assembly comprising one or more pore-subunit polypeptides sufficient to form a pore, wherein the pore comprises at least a first channel, and at least one of said pore-subunit polypeptides is a modified pore-subunit polypeptide comprising a pore-subunit polypeptide covalently linked to an exogenous sensing moiety capable of preferentially binding with a specific analyte; and detecting an electrical current through at least a first channel, wherein a modulation in current compared to a current measurement in a control sample lacking said analyte indicates the presence of said analyte in said sample.

2. The method of claim 1, wherein said electrical current is detected through a single channel.

3. The method of claim 1, wherein said electrical current is detected through at least two channels.

4. The method of claim 1, wherein said analyte is known.

5. The method of claim 1, wherein said analyte is unknown.

6. The method of claim 1, wherein said analyte is an oligonucleotide.

7. The method of claim 1, wherein the amount of said analyte in said sample is quantitated.

8. The method of claim 1, wherein the exogenous sensing moiety is a polymer.

9. The method of claim 1, wherein the exogenous sensing moiety is an oligonucleotide or a polynucleotide.

10. The method of claim 1, wherein the exogenous sensing moiety is a single stranded DNA molecule.

11. The method of claim 1, wherein the modified pore-subunit polypeptide is a pore-subunit polypeptide covalently linked to an oligonucleotide.

12. The method of claim 11 wherein the modified pore-subunit polypeptide is a staphylococcal alpha hemolysin pore-subunit polypeptide covalently linked to an oligonucleotide.

13. The method of claim 1, wherein the exogenous sensing moiety is an oligonucleotide and wherein the analyte comprises a polynucleic acid comprising a base sequence that is complementary to the exogenous sensing moiety.

14. A method of detecting the presence of an analyte in a sample, wherein the analyte comprises a polynucleic acid comprising a specific base sequence, the method comprising:

contacting said sample with a pore assembly comprising one or more pore-subunit polypeptides sufficient to form a pore, wherein the pore comprises at least a first channel, and at least one of said pore-subunit polypeptides is a modified pore-subunit polypeptide comprising a pore-subunit polypeptide covalently linked to an exogenous sensing moiety that is an oligonucleotide, wherein the oligonucleotide comprises a base sequence that is complementary to said specific base sequence of said analyte; and detecting an electrical current through at least a first channel, wherein a modulation in current compared to a current measurement in a control sample lacking said analyte indicates the presence of said analyte in said sample.

* * * * *

SEQUENCE LISTING

<160> NUMBER OF SEQ ID NOS: 14

<210> SEQ ID NO 1
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 1 cattcacc                                                                  8

<210> SEQ ID NO 2
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 2 ggtgaatg                                                                  8

<210> SEQ ID NO 3
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 3 tgacagat                                                                  8

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 4
acaaaatcca gacatagtta tctatcaata                                         30

<210> SEQ ID NO 5
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 5
acaaaatcca gacatagtta tctgtcaata                                         30

<210> SEQ ID NO 6
<211> LENGTH: 9
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(9)
<223> OTHER INFORMATION: N = C, G, A or T

<400> SEQUENCE: 6 gcattcnnn                                                                 9

```
<210> SEQ ID NO 7
<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: N = C, G, A or T

<400> SEQUENCE: 7 ngaatgc                                                                   7

<210> SEQ ID NO 8
<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: N = C, G, A or T

<400> SEQUENCE: 8 ntgaatg                                                                   7

<210> SEQ ID NO 9
<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: N = C, G, A or T

<400> SEQUENCE: 9 ngtgaat                                                                   7

<210> SEQ ID NO 10
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 10 attcacc                                                                   7

<210> SEQ ID NO 11
<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: N = C, G, A or T

<400> SEQUENCE: 11 ggtnaat                                                                   7

<210> SEQ ID NO 12
```

```
-continued

<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: N = C, G, A or T

<400> SEQUENCE: 12 ggtgnat                                                                      7

<210> SEQ ID NO 13
<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: N = C, G, A or T

<400> SEQUENCE: 13 cattcan                                                                      7

<210> SEQ ID NO 14
<211> LENGTH: 8
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: N = C, G, A or T

<400> SEQUENCE: 14 gntgaatg                                                                     8
```